(12) United States Patent
Ainsworth et al.

(10) Patent No.: US 7,450,686 B2
(45) Date of Patent: Nov. 11, 2008

(54) CONTAMINANT DETECTOR FOR FOOD INSPECTION

(75) Inventors: Teresa Ainsworth, Plymouth, MN (US);
Yuriy Bro, Shoreview, MN (US);
Frederick Cash, Maple Grove, MN (US); Gary Dickinson, Rogers, MN (US); Scott Eggerth, Saint Paul, MN (US); Tom Erb, Austin, TX (US);
Jeffrey Ferguson, Minneapolis, MN (US); David Gessner, Lino Lakes, MN (US); Bruce Herbes, Minneapolis, MN (US); Kevin Johnson, Zimmerman, MN (US); Sergey Moskalenko, Maple Grove, MN (US); Lorna Lockman, Coon Rapids, MN (US); Doug Schmidt, Harris, MN (US)

(73) Assignee: Thermofisher Scientific, Coon Rapids, MN (US)

( * ) Notice: Subject to any disclaimer, the term of this patent is extended or adjusted under 35 U.S.C. 154(b) by 41 days.

(21) Appl. No.: 11/664,603

(22) PCT Filed: Oct. 25, 2005

(86) PCT No.: PCT/US2005/038550

§ 371 (c)(1),
(2), (4) Date: Apr. 3, 2007

(87) PCT Pub. No.: WO2006/137919

PCT Pub. Date: Dec. 28, 2006

(65) Prior Publication Data

US 2008/0118026 A1 May 22, 2008

Related U.S. Application Data

(60) Provisional application No. 60/623,461, filed on Oct. 29, 2004.

(51) Int. Cl.
*G01N 23/04* (2006.01)

(52) U.S. Cl. ........................................ 378/57; 378/199

(58) Field of Classification Search .................. 378/57, 378/199–200, 68–69, 141, 198
See application file for complete search history.

(56) References Cited

U.S. PATENT DOCUMENTS 4,791,655 A * 12/1988 Nagata et al. .................. 378/57

(Continued)

*Primary Examiner*—Hoon Song
(74) *Attorney, Agent, or Firm*—David George Johnson

(57) ABSTRACT

A contaminant detection machine (1) including a conveyor (3) which causes an object under inspection (79) to pass through a plane (48) of emitted x-ray radiation. The plane is generated by an x-ray tube (55) that emits a lateral beam, thereby permitting the distance (88) between the x-ray tube and the object under inspection to be reduced. A photo diode arch mounting assembly (104) is placed above the object under inspection and is mated to a collimator assembly (125) that also serves as the mounting bracket for the x-ray generation assembly (38), thereby preserving optical alignment between the photo diode detector array (28) and the emitted x-ray plane (48). The detector array (28) scans the object under inspection (79) so as to produce a continuous series of discrete lines, each line being analyzed by an image processing unit (116) to determine the presence or absence of a contaminant. The conveyor (3) passes over a pair of slider bed surfaces (155, 156) which are mounted in a hinged manner such that the leading edge (168) of one surface (156) is parallel to and spaced apart from the trailing edge (172) of the other surface (155), thereby creating a gap that is coplanar with the collimation slot (129) and the emitted x-ray plane (48). Each bed surface (155, 156) is rigidly constrained within open ended mounting brackets (159, 160, 161 and 162) yet can be removed by hand without the use of tools. Similarly, the conveyor (3) is supported by a roller assembly (182) that includes a tracking block (142) and pivot pin (143) which permits the roller assembly to be mounted to and removed from flip up mounts (151, 152) by hand and without the need of tools. Graphical user interfaces (249, 260, 261, 266, 275, 282 and 288) permit a user to operate the machine (1) by means of a liquid crystal display touch screen (20).

8 Claims, 22 Drawing Sheets

U.S. PATENT DOCUMENTS

| | | | |
|---|---|---|---|
| 5,260,982 A * | 11/1993 | Fujii et al. | 378/87 |
| 6,335,960 B2 | 1/2002 | Knigge et al. | |
| 6,584,170 B2 * | 6/2003 | Aust et al. | 378/57 |
| 2002/0071524 A1 * | 6/2002 | Renkart et al. | 378/199 |

* cited by examiner

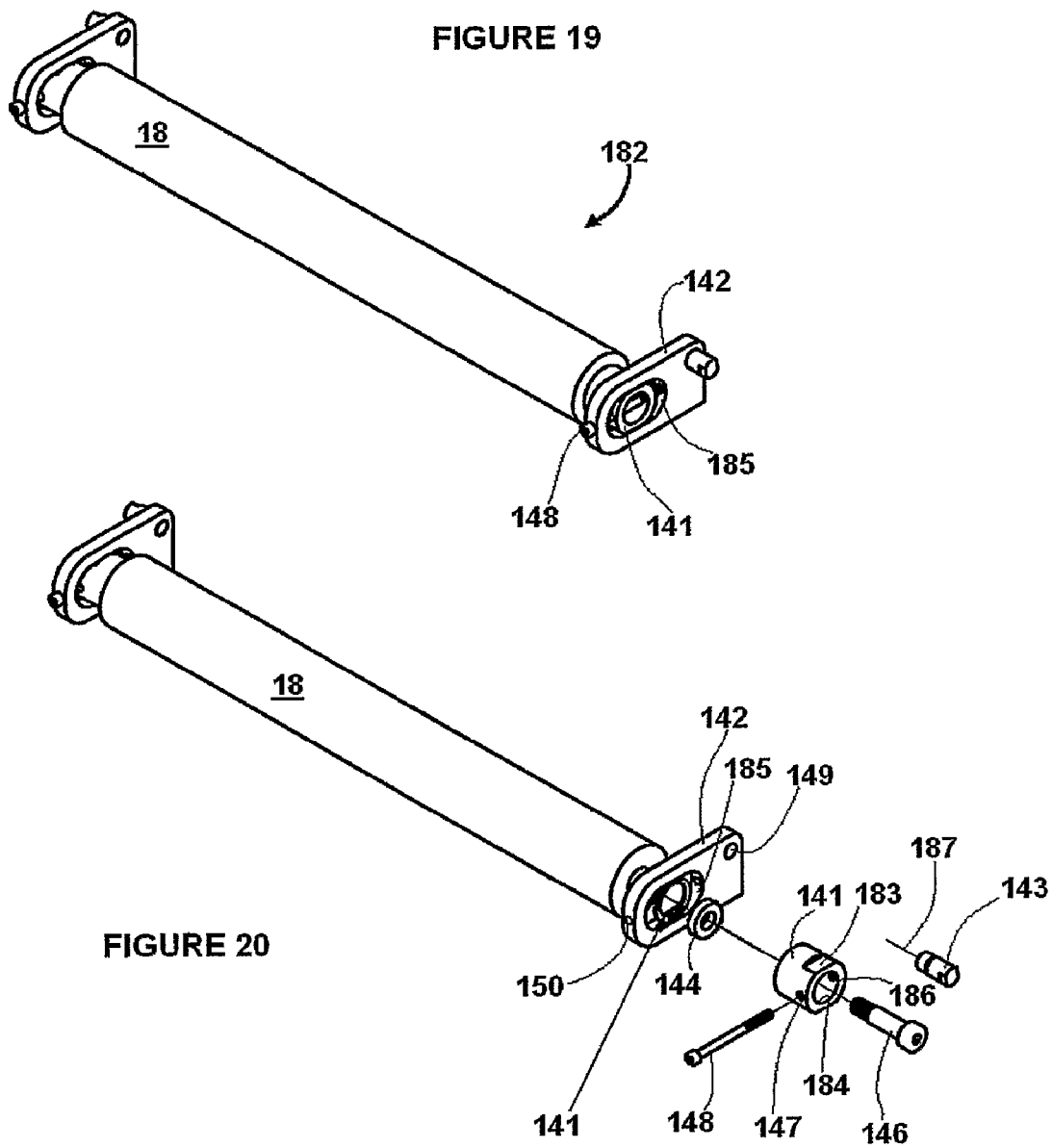

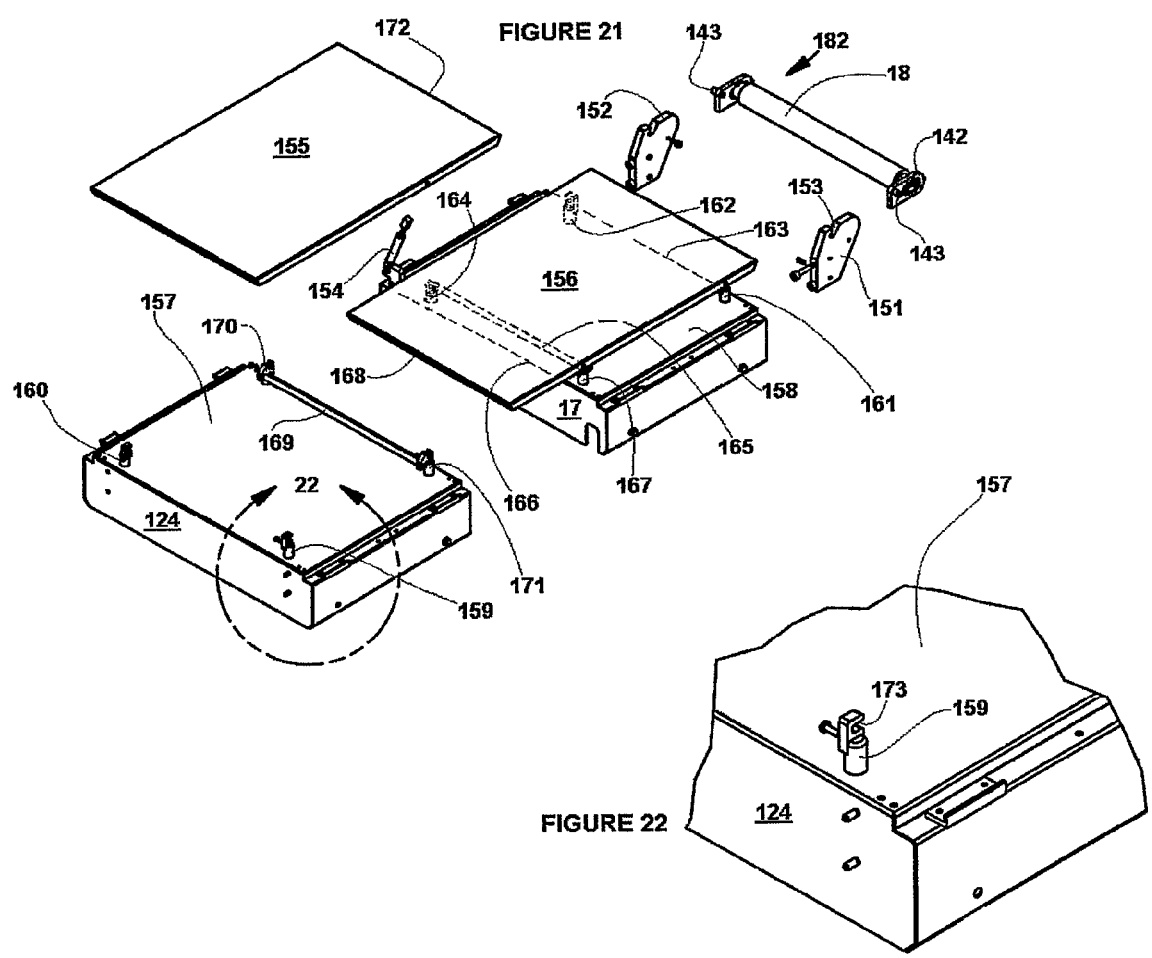

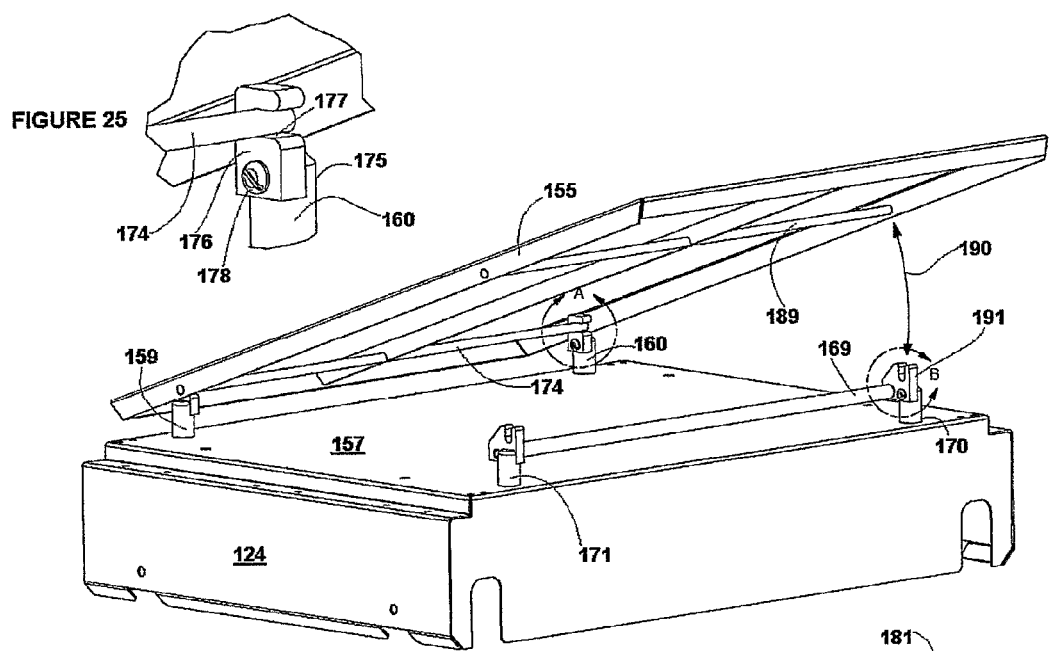
FIGURE 25
FIGURE 23
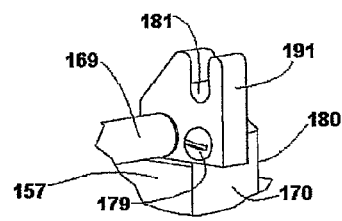
FIGURE 24

CONTAMINANT DETECTOR FOR FOOD INSPECTION

This patent application claims priority based on U.S. Provisional Patent application Ser. No. 60/623,461, filed on Oct. 29, 2004.

FIELD OF THE INVENTION

The present invention relates generally to the field of detecting foreign material within an item undergoing inspection, and more particularly to a detecting apparatus that irradiates the inspected item with X-Rays.

BACKGROUND OF THE INVENTION

Conventional metal detectors often fail when detecting metal contaminants in products that incorporate metal as part of the product or the associated packaging. Examples of such products include foods encased in a metal foil, foods residing in aluminum cups, bowls or trays, foods with metal foil freshness seals, and foods fully or partially covered with thin metal lids. Other foreign materials such as bone, glass and stone may also be present in food items. X-rays have been used to irradiate food items in an attempt to detect foreign matter. An example of such a device is disclosed in U.S. Pat. No. 6,512,812, entitled X-RAY FOREIGN BODY DETECTOR, issued on Jan. 28, 2003 to Watanabe.

In the typical x-ray detector there are multiple settings which are optimized for the detection of a certain class of expected contaminant. When the expected contaminant is metal, which has a relatively high x-ray absorption rate in comparison to the surrounding food item, the level of x-ray emission and the corresponding detector sensitivity can be set relatively easily to take advantage of the contrast between the food and any metal that may be present. However, if such a metal optimized setting is used, then the detection of bone or glass, as well as any relatively thin or small metal objects, is much less reliable. A proposed solution to this problem is to use multiple x-ray sources to irradiate the item undergoing inspection. An example of a multiple source x-ray inspection device is disclosed in U.S. Pat. No. 6,370,223, entitled AUTOMATIC DETECTION OF BONE FRAGMENTS IN POULTRY USING MULTI-ENERGY X-RAYS, issued on Apr. 9, 2002 to Gleason et al.

Existing foreign object detectors typically function by emitting relatively narrow angle x-rays, that is, the emitted x-rays reside within a plane or relatively narrow cone. A narrow angle x-ray source prevents radiation in unwanted directions and is necessary for safety reasons, but such a source consumes a relatively high amount of power and is relatively expensive. Further, the narrow angle is achieved by utilizing longitudinal radiation from the x-ray transmitting tube, which is a relatively small portion of the total available radiation. The lateral radiation emitted by the tube is not utilized. An example of a detection device using a narrow angle x-ray emitter is disclosed in U.S. Pat. No. 5,428,657, entitled X-RAY MONITORING SYSTEM, issued on Jun. 27, 1995 to Papanicolopoulos et al.

All of the devices disclosed in the previously cited patents share a common construction characteristic insofar as the x-ray emitter is placed physically above a moving conveyor and the x-ray sensor is placed below the conveyor. This arrangement necessarily increases the cost of the resulting machine for several reasons. First, an x-ray emitter requires a substantial power source which must be routed to the emitter location. Second, the heat producing x-ray emitter is relatively difficult to cool in an enclosed, elevated location. Third, the x-ray emitter is necessarily spaced relatively far from the object under inspection because it must be well above the aperture through which the conveyor enters and the aperture itself is as large as possible to accommodate larger test items. This mechanical arrangement results in a reduction in the amount of radiation actually entering or impinging upon any item being inspected at fixed flux intensity, thus requiring an increase in the absolute flux density needed to penetrate denser objects. Fourth, the x-ray detectors reside beneath the conveyor where they are subject to additional contamination and are relatively difficult to cool, isolate from vibration and to service.

Additional problems encountered in a real world food processing assembly line process include the accumulation of contaminants on the test item conveying mechanism. These contaminants typically include remnants of the foodstuffs under test as well as lubricants and particulates present in the food processing environment. While the signal processing aspects of existing x-ray detection devices may be quite exotic, the cleanliness and serviceability or the conveyor belt is often primitive and results in downtime that renders the relatively high reliability of the electronics irrelevant to the total real world duty cycle of the machine.

SUMMARY OF THE INVENTION

The present x-ray based contaminant detector addresses the disadvantages of prior art devices. In particular, the present invention is a contaminant detector for food inspection that utilizes lateral emission x-ray technology and which includes an integrated conveyor that passes the product under test near the x-ray emitting source. The machine is a conveyor line scan x-ray system that can be produced with different aperture sizes and conveyor speeds and at a relatively low cost. The present contaminant detector uses a wide-angle x-ray emitting source to generate the necessary x-ray radiation for penetrating the object under inspection, thereby permitting detection of a contaminant. Use of a wide transmission angle results in reduced production costs by eliminating the expense associated with a narrow angle radiation source.

Product learning algorithms automatically determine nominal product characteristics and substantially reduce the need for operator assisted machine initialization activities. The operator typically needs only to pass a known nominal product through the machine in order to teach the machine the characteristics of an acceptable product. The controls are thus simplified in comparison to existing metal detectors, thereby eliminating or substantially reducing errors caused by the incorrect setup of operating parameters. The simpler design of the present contaminant detector produces a machine having relatively greater reliability and a longer life expectancy than other x-ray based food inspection machines The primary function of the present invention is to provide for the detection of relatively dense contaminants within food or other products. In an alternate embodiment, quantitative data is identified, permitting identification of the type of contaminant as well as signaling the absence or presence of a particular contaminant. X-ray scans are used to collect density maps of the Object Under Inspection (OUI) in order to allow discrimination of contaminant presence from both the food and the food package.

The present invention is intended primarily for metal detection applications where the type of contaminant, product, or the product packaging precludes the use of a conventional metal detector, such as, for example, when inspecting food residing in packages containing metal. Several advantages are offered by the characteristics inherent in the present invention. By using X-Rays for detection, there is no metal free zone restriction. For products that exhibit high and variable product effect with other metal detectors due to their conductivity, contaminant detection by x-ray provides the same sensitivity as is possible when detecting contaminants in a conventional, low conductivity product. The present invention permits a relatively lower cost per item inspected than a conventional x-ray based inspection machine. The cost per item is reduced by the use of a novel, relatively low power x-ray generation system and power supply, thereby reducing the cooling costs present in higher power x-ray inspection systems.

The OUI is inspected for contaminants by analyzing the differential gray scale pixilated representation of the relative x-ray absorption of the OUI within the area under inspection. This analysis interprets the presence of a contaminant, typically via a threshold determination or comparison means. Other analysis techniques may be employed as well, based upon the severity or difficulty of the specific product being inspected.

X-Rays penetrate materials based upon the energy level of the incident ray. Higher energy rays, typically discussed in units of kilovolts [kV], which are needed to accelerate electrons from cathode to anode within the x-ray tube, penetrate deeper than lower energy rays. The electron beam filament current determines the number of x-ray photons generated. The magnitude of the x-ray energy level bears a relationship to the contrast available in the resulting density image of the scanned object. The magnitude of the electron beam filament current corresponds to the brightness or gain of the resulting density image. This means that higher energy x-rays will pass more energy through denser areas than lower energy rays. High energy x-rays will, however, pass nearly or substantially completely through less dense areas of the OUI. The energy level and electron beam filament current are the variable controls used to set or adjust the quality of the scanned image density map.

Generating and processing a series of linear scans of the OUI accomplishes the contaminant detecting x-ray scanning process. An array of photodiodes is exposed to illumination, in this case the emitted x-rays, and the exposure is sampled in the time domain in order to create and build an image. The x-rays that are able to pass through the OUI produce the density image. The resulting image is a density map of the OUI.

In the present invention the x-ray source and detector locations are altered when compared to existing x-ray based detection systems. The number of photons incident upon the x-ray detectors per unit area, known as the x-ray flux, decreases as the square of the distance from the x-ray source. By altering the positions of the source and detector, and thus having the x-ray source pointed generally upward, the OUI is closer to the source and it becomes possible to image products after the emitted x-rays have traveled a relatively smaller distance, thereby requiring significantly less x-ray generation for the same effective flux. This physical arrangement allows the use of an x-ray tube that is relatively smaller and which has lower power consumption, thus permitting the use of a less expensive cooling system.

In the present invention the density image that results from the scanning operation is not as clear a representation of the OUI as might, for example, be created by a baggage scanner at an airport screening location. The present arrangement of the x-ray source with respect to the x-ray detectors does not necessarily allow clear, optical quality imaging, nor is it necessarily precluded. The scanning process gathers information that is useful for the purpose of identifying dense contaminants rather than being applicable to tasks such as counting the number of cookies in a package, determining the position of a spoon in a lunch pack, seeing if a carrot is broken or performing other measurements relating to product quality.

An automated learning procedure is performed on a per product basis. The learning procedure determines what type of signal filtering is required for contaminant detection and also determines the optimum x-ray power level settings. Automated learning parameters are typically determined primarily by conveyor belt speed and aperture size. Field calibration is required to compensate for zero signal level and absolute gain differences between the photodiodes present in the detector array. The present machine performs a diode calibration based on a stored calibration file that is assigned for each class package to be inspected.

The present invention includes a product set up menu that specifies the operational details needed to detect a specified level of contaminant. In one embodiment of the invention, product classes within which a contaminant may be successfully detected include products with foil tops or freshness seals, foil pans, foil boxes, plastic trays with foil packs, stapled bags, packages having a metal top or bottom, packages containing bone, packages containing stone, packages containing glass, continuous bulk product and packages containing arbitrarily dense contaminants.

The detection processes of present invention do not vary with the class of product under inspection. One issue addressed by the present invention is the qualification of the device by means of a known standard based on the sensitivity, range and the type of foreign object (FO) being detected, and the correlation of the qualification performance to the subsequent performance of the system to an unknown and untested real world package. The specified performance of prior art devices may not correspond well to the actual performance due to a variety of factors, including packaging type, product density variation, package segmentation, or multiple object presence, especially in ready to eat meal products. The detection processes of the present invention include a sequence of algorithms or filters which process the scanned x-ray image, determine detection thresholds, and announce or display results. Certain products may require more of these filters than others. As more filters are utilized, more computation time is required and consumed. The top speed of the present system is therefore dependent on the amount of filtering required. The present invention may operate in alternate filtering modes. In one embodiment, the device preselects those filters and algorithms as appropriate for the class of product in order to optimize the compromise between conveyor speed and detection accuracy. In an alternate embodiment, two particular filters represent a default mode of operation and are always applied in the same order.

In one embodiment, the present invention may utilize three contaminant type classifications. For each contaminant type there is typically a unique dimensional detection limit and maximum conveyor operating speed that is dependent on the aperture size through which the OUI is transported. Detectable contaminant size is characterized in terms of being equivalent to a stainless steel sphere having a known size. For the present invention the minimum detectable contaminant size for metal is an approximately one millimeter sphere, while for glass and stone the equivalent sphere size is approximately three millimeters.

BRIEF DESCRIPTION OF THE DRAWINGS

FIG. 19 is a perspective view of the idler roller assembly of the machine of FIG. 1;

FIG. 20 is an exploded perspective view of the idler roller assembly depicted in FIG. 19;

FIG. 21 is an exploded perspective view of the slider bed mounting configuration of the machine of FIG. 1;

FIG. 22 is a detailed perspective view taken at region 22 of the slider mount depicted in FIG. 21;

FIG. 23 is a perspective view of the mounting arrangement of the slider bed depicted in FIG. 21;

FIG. 24 is a perspective view of the slider bed latch detail B depicted in FIG. 23;

FIG. 25 is a perspective view of the slider bed hinge detail A depicted in FIG. 24;

DETAILED DESCRIPTION OF THE INVENTION

Figure 1:
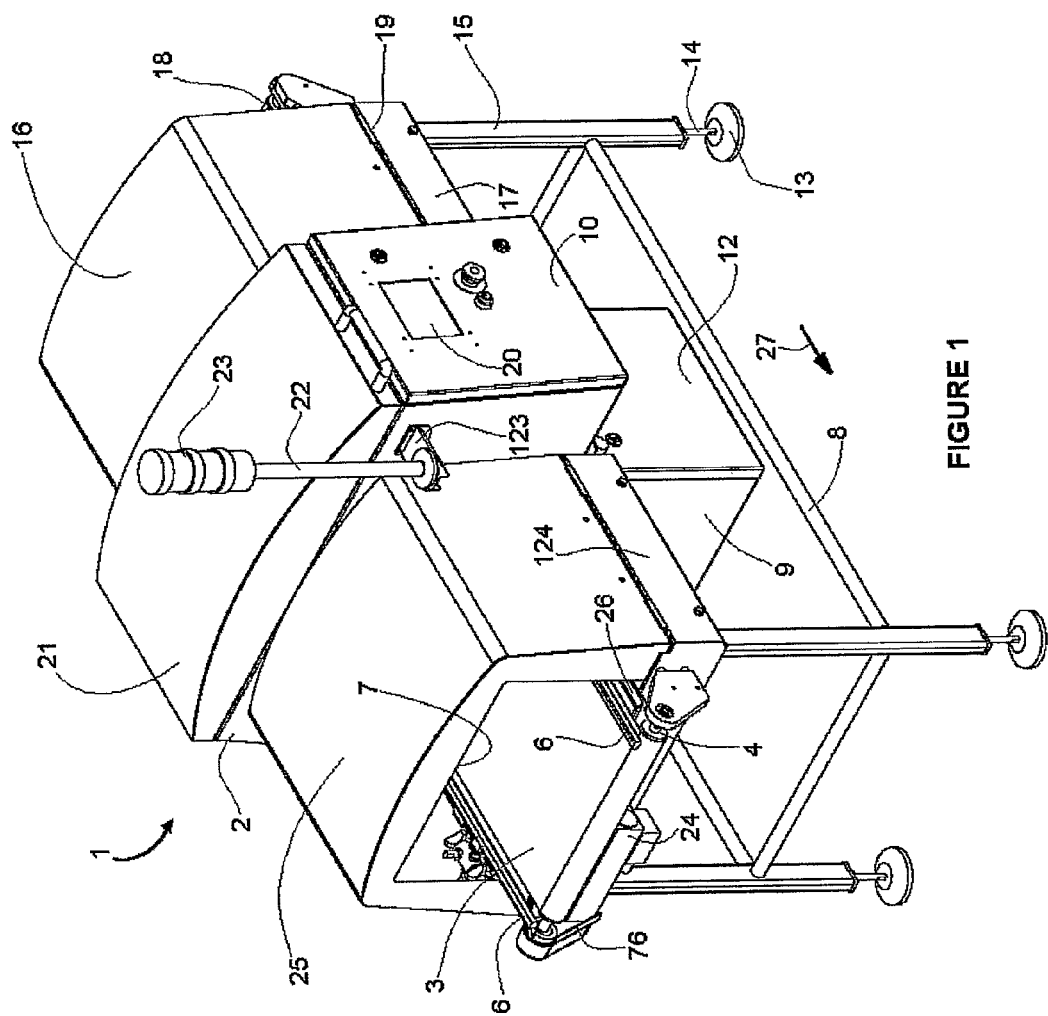
FIG. 1 is a perspective view of a contaminant detection machine constructed according to the principles of the present invention.
Figure 18:
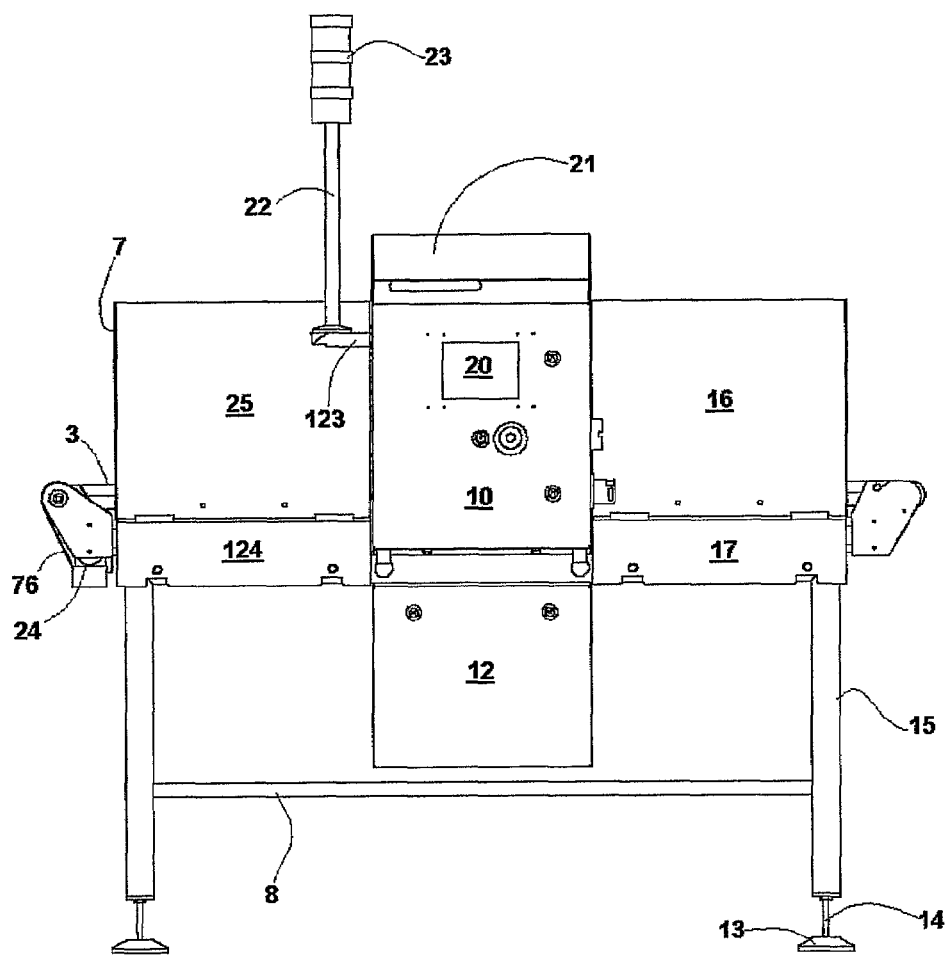
FIG. 18 is a right front elevation of the machine of FIG. 1.

As seen in FIGS. 1 and 18, the contaminant detector 1 is a conveyor line scan x-ray inspection system designed primarily for contaminant detection in packaged products. The contaminant detector 1 provides a functional quality control system in a factory or product processing facility. The contaminant detector 1 is intended for use where conventional metal detectors fail, typically when detecting dense contaminants such as glass, bone, stone, and plastic or metal in products that incorporate metallic materials as a part of the product packaging. Examples of such products include metal foil encased foods, foods in aluminum tins, cans or trays, foods with metal foil freshness seals, and selected foods with thin metal lids, or items, such as lettuce, for example, or other foods without metal packaging but having high product effect with respect to conventional metal detectors.

The contaminant detector 1 includes an x-ray generation unit housing 9 which contains various internal components accessible via a hinged door 12. X-rays are part of the electromagnetic radiation spectrum which includes radio waves, microwaves, infrared, the visible spectrum, ultraviolet and gamma radiation. X-rays have a short wavelength on the order of $10^{-10}$ meters. X-rays are also known as ionizing radiation because of the way they interact with matter. X-rays are produced within the x-ray generation unit 9 by means of a cathode ray tube which causes electrons to hit a metal target within the tube at a high speed and thereby generate x-rays. Over ninety five percent of the energy supplied to the cathode ray tube is converted to heat. The entire tube is immersed in oil, shielded in lead, and contained in a tank. This ensures that the x-rays are contained within the tank, except for a controlled beam used for detection.

The controlled beam is emitted so as to travel toward an inspection chamber 2. The interior of the inspection chamber 2 is accessible via hinged panels 10 and 21. Within the inspection chamber is an array of photodiodes which detect the x-rays that are able to travel through any objects that may reside between the x-ray generation unit housing 9 and the photodiodes. X-rays are capable of penetrating through dense materials. The depth of penetration is determined in part by the density of the material. The depth of penetration is an important parameter because it permits differences in product densities to be determined.

The products being inspected are placed in the path of the emitted x-rays by means of a conveyor belt 3 which extends between a driven roller 4 and an idler roller 18. The driven roller 4 is driven by a motor 24 which operates a belt 76. An optional pair of guide rails 6 prevents the product or object under inspection (OUI) from straying off the belt 3. The OUI passes through an aperture 7 formed within the x-ray shield 25. The belt 3 and the OUI are supported by and travel over a pair of slider beds 26 which are mounted on slider bed frames 124 and 17. The OUI travels in the direction indicated by arrow 27, entering the inspection chamber 2 from the x-ray shield 16 and exiting the inspection chamber 2 toward the x-ray shield 25.

Operation of the contaminant detector 1 is accomplished by means of a data processing module 10 which includes a display panel 20. Whenever the x-ray generation unit 9 is actually emitting x-rays, a lamp 23, supported by post 22 mounted on bracket 123, is illuminated. The slider bed frames 124 and 17, as well as the x-ray generation unit 9 and inspection chamber 2, are supported by a framework 8 which includes four legs 15. Each leg 15 has an adjustable leveling post 14 which terminates at a footpad 13.

Figure 2:
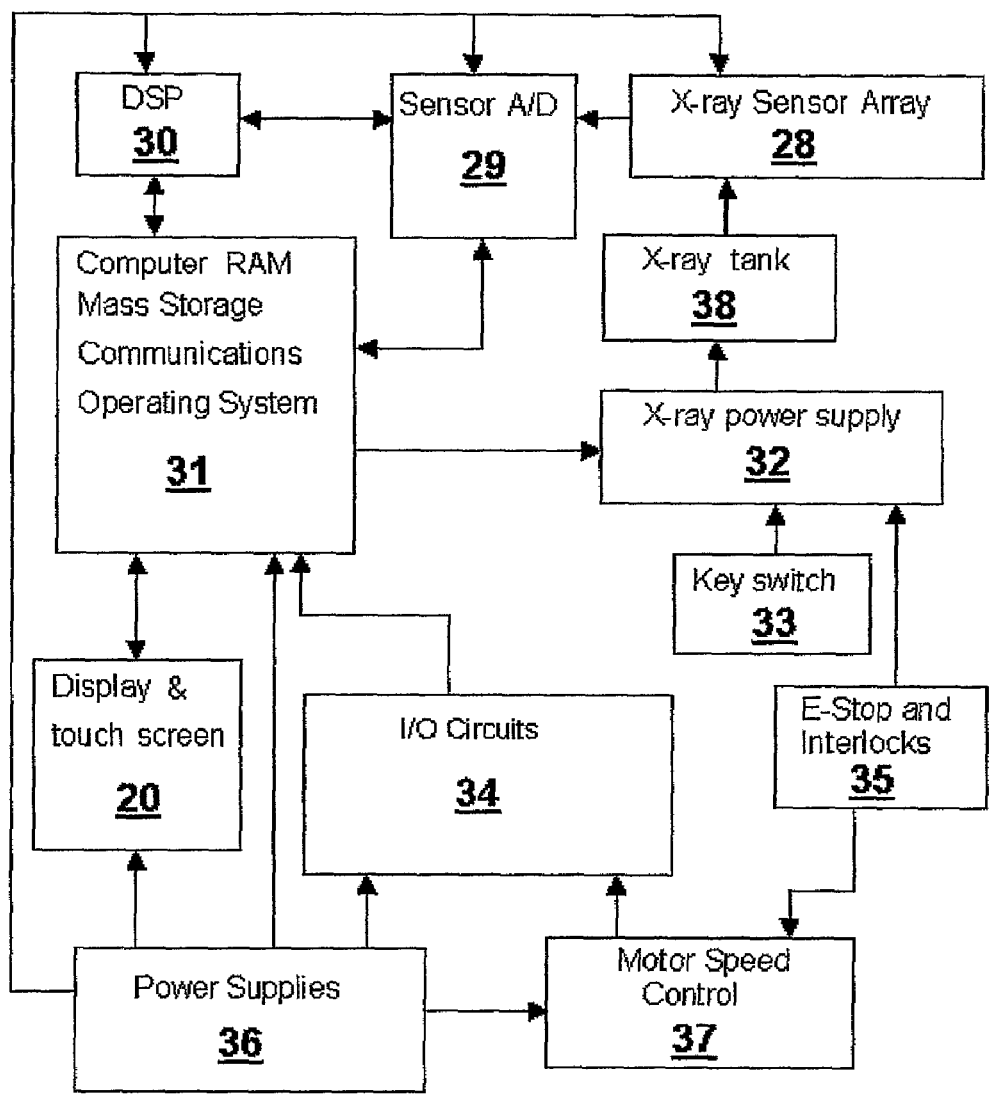
FIG. 2 is a system diagram of the machine depicted in FIG. 1.

Referring also to FIG. 2, the general contaminant detector system operation may be understood. X-rays are emitted from the x-ray tank assembly 38 residing within x-ray generation unit 9 and are detected by the x-ray sensor array 28 which is housed in the inspection chamber 2. The raw analog sensor array data is converted into digital form suitable for further processing by the A/D converters 29. The digitized sensor array data is then processed by digital signal processor (DSP) 30 to determine the actual presence or absence of a contaminant. The DSP 30 is a software driven device capable of applying various filtering algorithms and protocols to digital input data received from the x-ray sensors 28.

Figure 29:
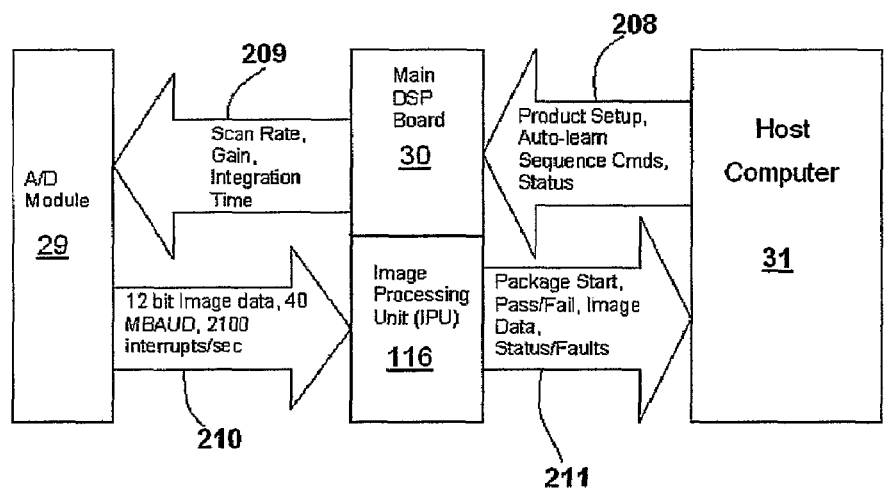
FIG. 29 is a block diagram of the digital signal processing firmware of the machine depicted in FIG. 1.

Referring also to FIG. 29, a host computer 31 is seen to control the operation of and provide instructions to the DSP 30. The host computer 31 defines product setup parameters, automatic learning protocols, sequence commands and status information 208. Based on the instructions received from the computer 31, the DSP 30 is then able to define particular processing parameters such as the OUI image scan rate and the appropriate filter integration time 209 which is then forwarded to the sensor A/D module 29. The A/D module 29 produces image data, which is typically twelve bit image data delivered to the image processing unit 116 at a data transmission rate of sixty mega baud and 2,100 interrupts per second. The image processing unit 116 further analyzes and processes the results produced as a result of the DSP setup parameters and the A/D module raw data. The IPU 116 delivers inspection related information 211, and may include data such as package start, pass/fail, image data and status, to the computer 31.

The detection threshold used by the IPU 116 represents a number between zero and one hundred percent, with zero representing black and one hundred representing white. When an x-ray picture of the OUI is taken the image is produced because some portions of the OUI absorb some of the x-rays and cast a shadow on the photo diode sensors 28. The filter threshold is the minimum response received from an uncontaminated product. Contaminants are typically denser than the product and produce a lower threshold. The IPU 116 includes several different types of filters that are used to enhance the detection process by increasing image contrast, reducing the effects of noise, amplifying sudden changes in product density, or masking dense package edges. Many different types of filters may be used. The simple filter finds large contaminants that are significantly denser than the product being inspected The gradient filter is useful for finding small contaminants and for reducing the effects of gradual changes in product thickness. The side edge mask filter masks the edges of products such as aluminum cans, cardboard boxes and aluminum pie pans having rolled or folded edges that can produce images with distinct dark bands surrounding the OUI perimeter. The side edge mask filter is used if there are dark edges present on the OUI container, and is applied prior to the use of other filters. The side edge mask examines less than the entire OUI and can miss contaminants located near the OUI edge. The gamma filter finds contaminants that are slightly denser than the product being inspected and is also capable of finding dimensionally small contaminants. The contrast-sharpening filter increases image contrast by subtracting a blurred version of the image from the original image. The contrast sharpening filter locates small contaminants in an OUI that does not have any sharp edges and provides a two dimensional alternative to the gradient filter. The enhanced gradient filter combines contrast stretching and the gradient filter to create another filter, making the enhanced gradient filter less sensitive to noise in the image.

The computer 31 receives user input from and supplies system information to the display panel 20. Various other Input/output (I/o) circuits 34 including devices such as photo sensors, conveyor velocity sensors, switches and relays are also coupled to and to varying extents controlled by the computer 31. One device linked to the I/o circuitry 34 is the motor speed control 37 which controls the operation of conveyor motor 24.

All of the various devices and circuits, with the exception of the x-ray tank assembly 38, receive their appropriate voltage and current requirements from the power supply 36. The x-ray tank assembly 38 requires a dedicated high voltage supply 32, capable of applying a plate voltage on the order of eighty kilovolts. The x-ray power supply 32 is housed within the x-ray generation unit 9. The actual voltage supplied to the x-ray tank assembly 38 by power supply 32 is controlled by the computer 31 and is based on the type of OUI and contaminant expected to pass through the aperture 7. An operator must use key switch 33 in order to activate the power supply 32, and various safety interlocks and emergency stop circuits 35 must also be properly engaged. Opening the hinged access lid 21 of the inspection chamber 2, for example, will deactivate both the power supply 32 and the motor speed control circuit 37.

Figure 3:
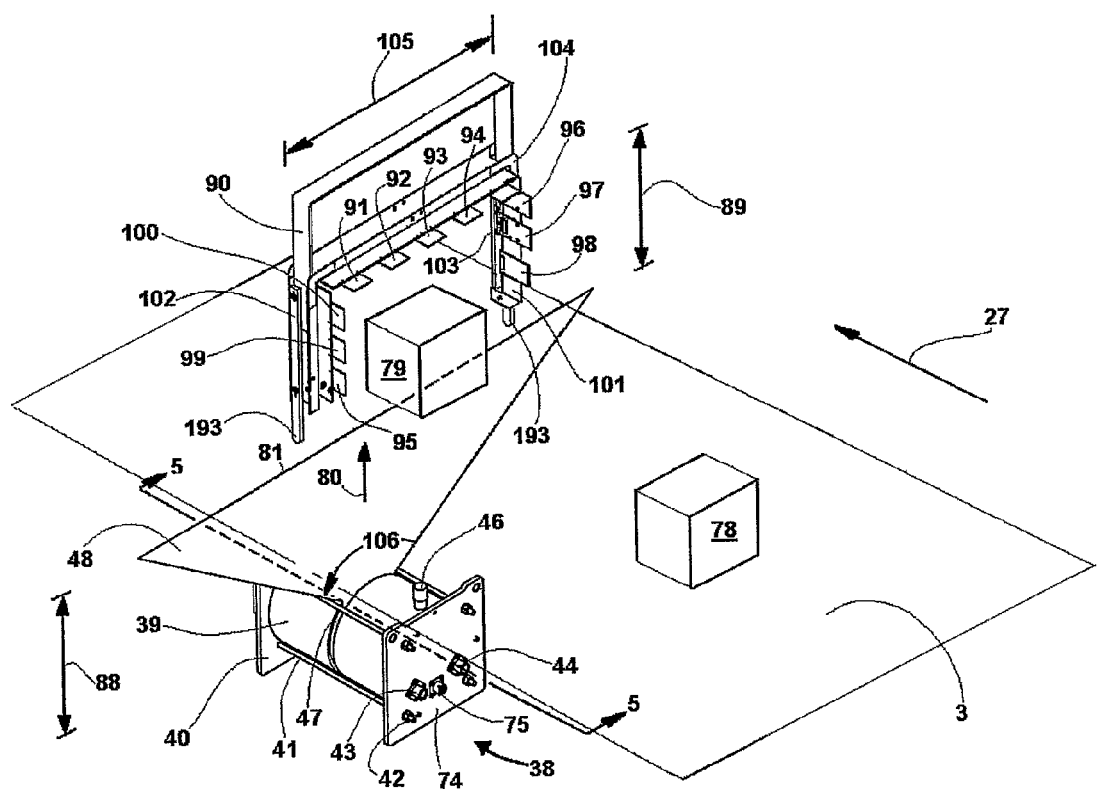
FIG. 3 is a perspective view of the x-ray tube tank assembly and its relationship to the conveyor and photodiode x-ray detector of the machine depicted in FIG. 1.
Figure 4:
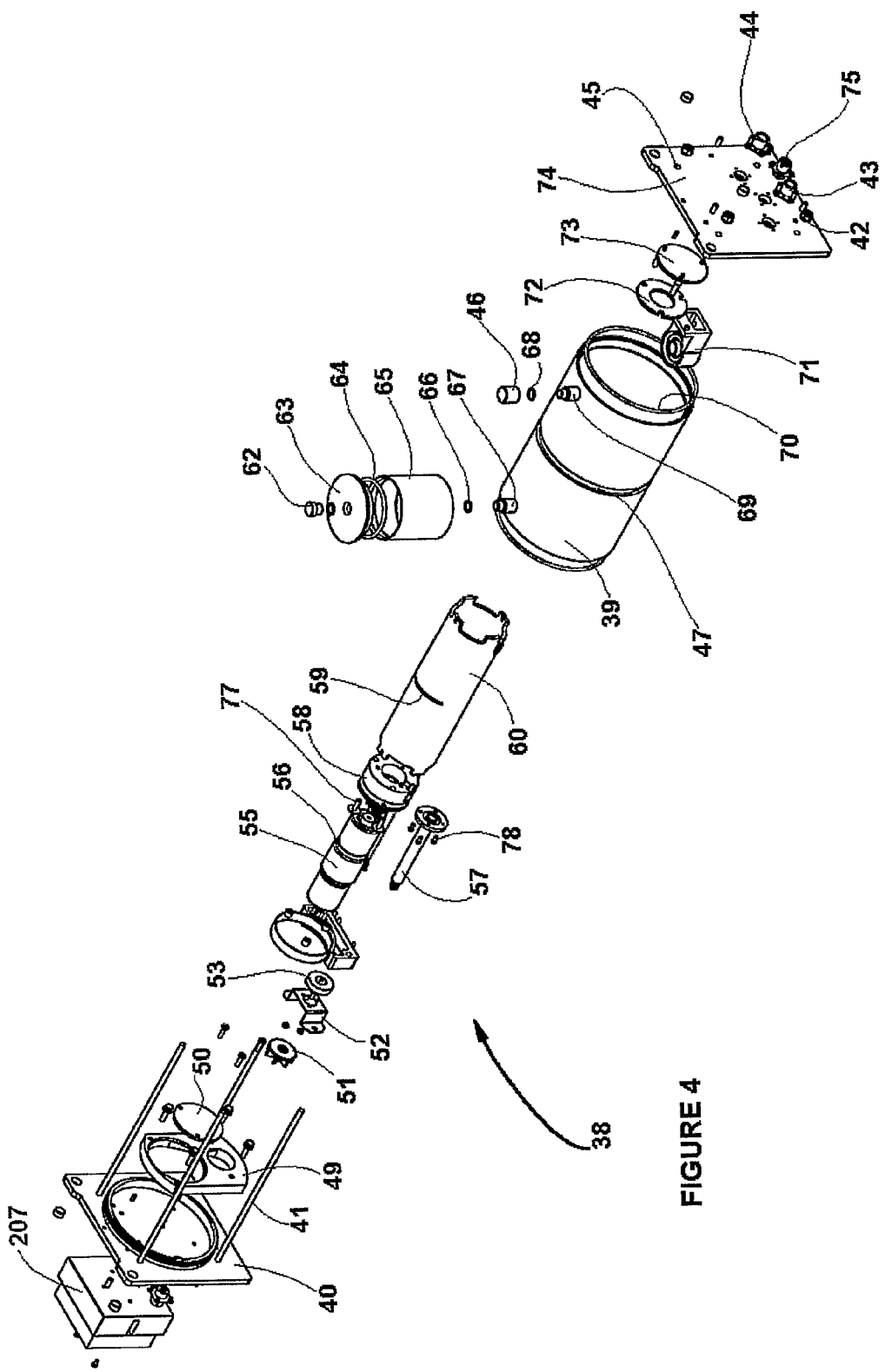
FIG. 4 is an exploded perspective view of the x-ray tube tank assembly depicted in FIG. 3.
Figure 5:
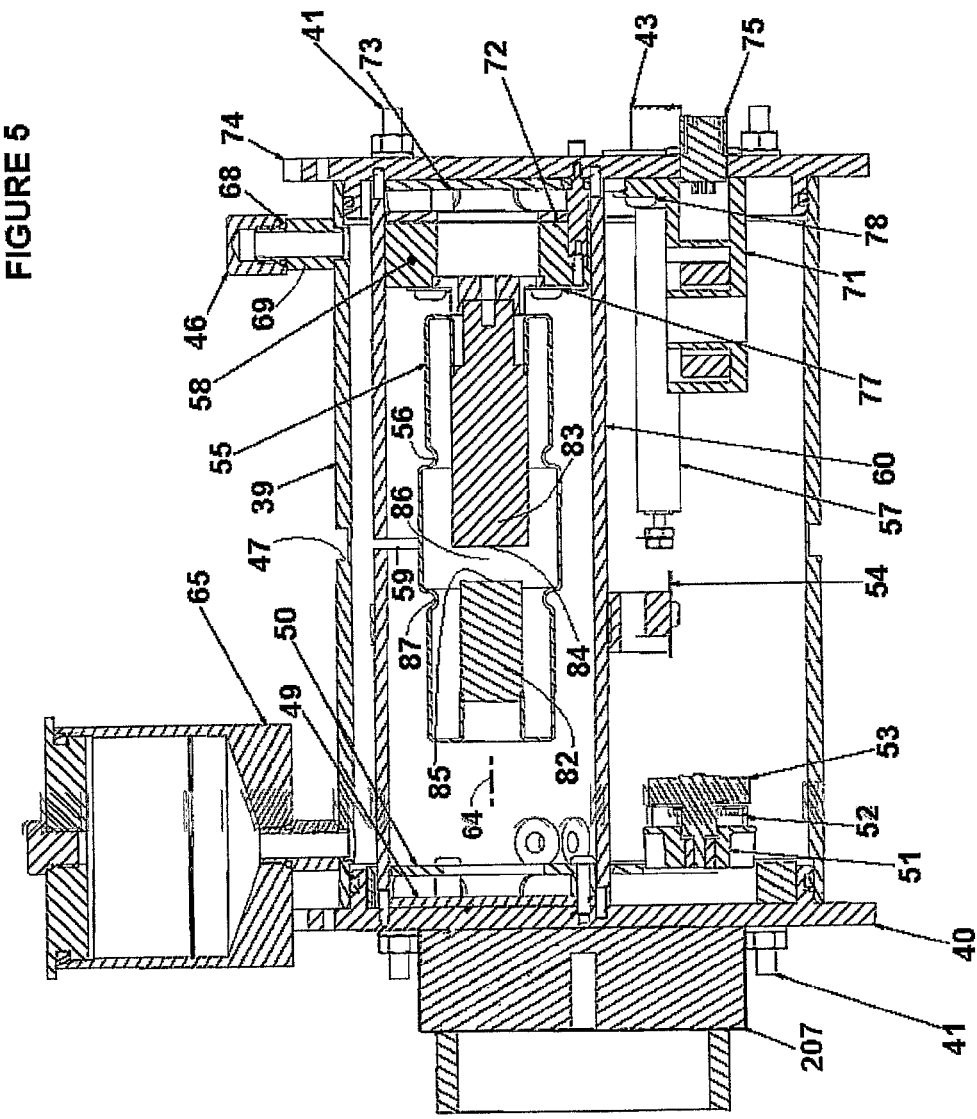
FIG. 5 is a sectional view of the x-ray tube and tank assembly taken along the line 5-5 in FIG. 4.
Figure 7:
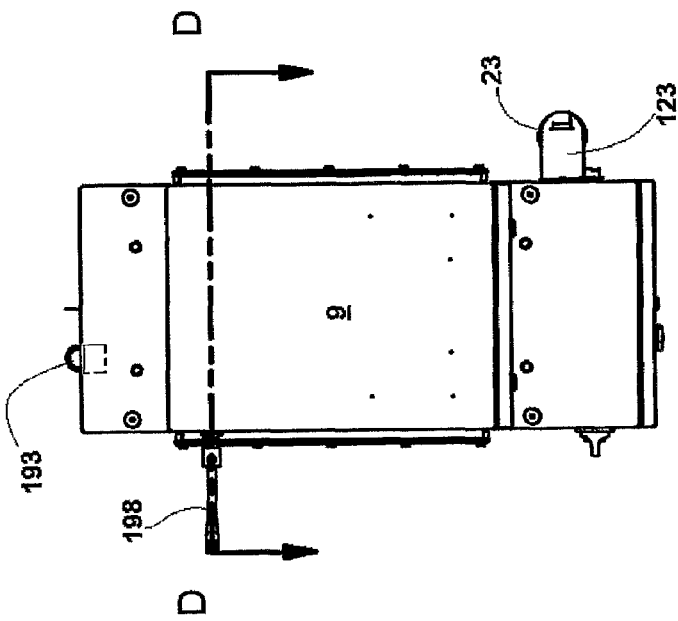
FIG. 7 is a bottom plan view of the machine depicted in FIG. 1.
Figure 6:
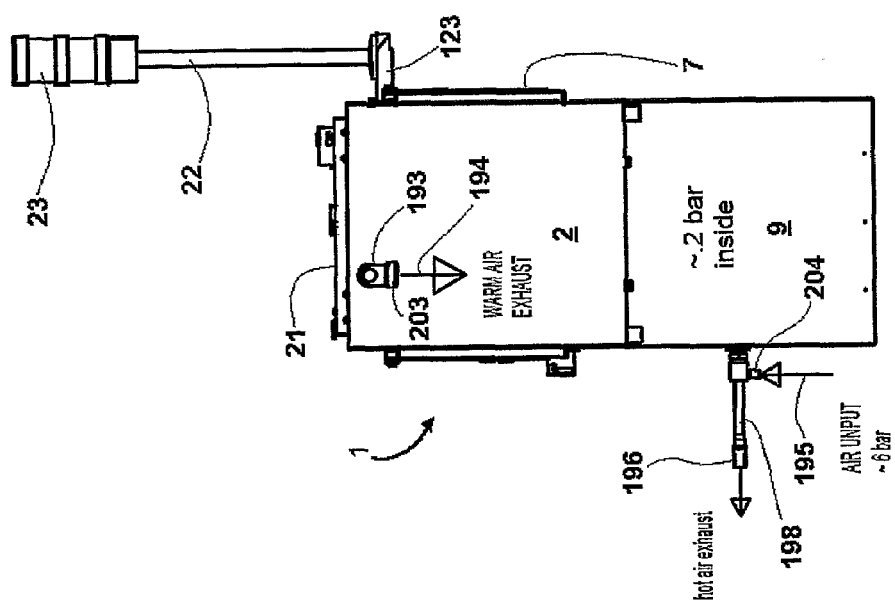
FIG. 6 is a rear elevation view of the machine depicted in FIG. 1.
Figure 12:
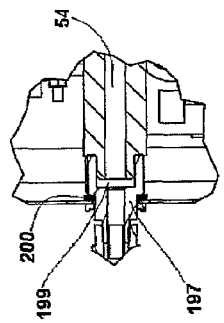
FIG. 12 is an enlarged view of the region E identified in FIG. 8.
Figure 8:
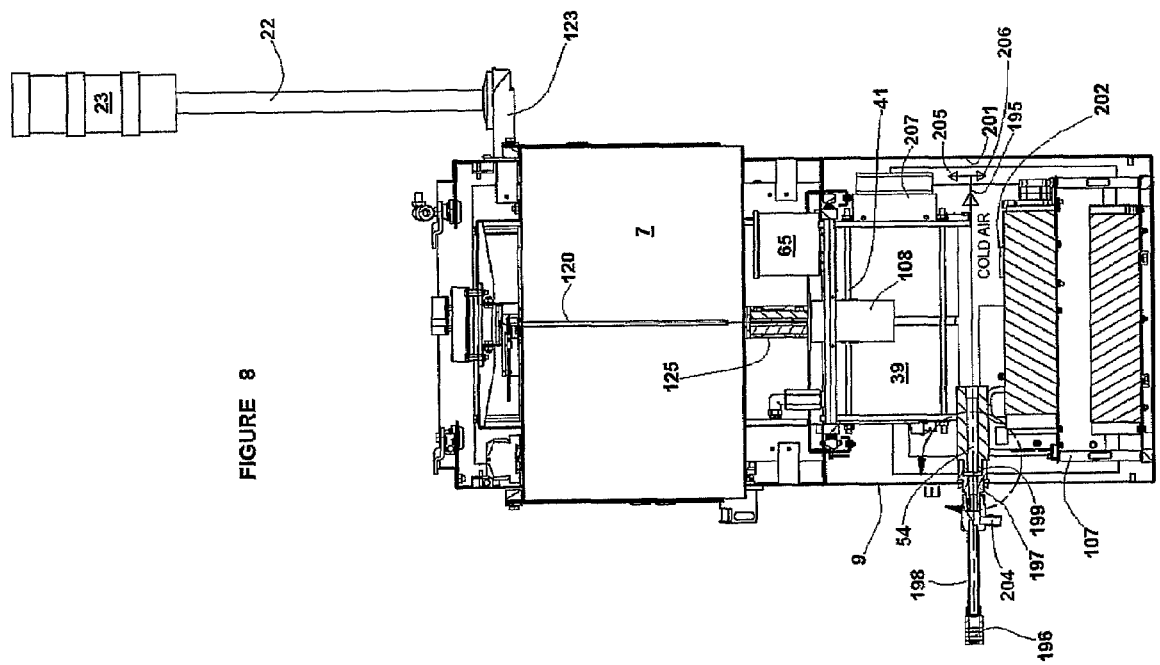
FIG. 8 is a sectional view taken along the lines D-D in FIG. 7.

Referring also to FIGS. 3, 4 and 5, the configuration of the x-ray tank assembly 38 that is housed within the x-ray generation unit 9 can be appreciated. As best seen in FIG. 3, the tank assembly 38 resides in a position that is below the conveyor 3. As seen in FIGS. 4 and 5, the tank assembly 38 includes an x-ray emitting tube 55 which includes a glass envelope that provides a vacuum for the electron beam generated within the tube. In the x-ray tube 55, electrons are emitted from a heated filament by a process called Schottky emission. This is thermionic emission, enhanced by a strong electric field near the filament that is produced by the voltage difference between the anode 83 and the cathode 82 of the tube 55. After they leave the filament, electrons are emitted from the filament in all directions in a transverse plane. Some of the emitted electrons travel at high speed toward a metal target which is the surface 84 of the anode 83, the collision with the surface 84 generating x-rays. Other emitted electrons strike portions of the cathode surface 85, contributing to its radiated heat load. Over ninety five percent of the energy supplied to the tube 55 by the x-ray power supply 32 is converted into heat. The mounting plate 74 is adjacent to the anode 83 of the tube 55, while plate 40 is adjacent to the cathode 82 of the tube 55.

The x-rays that are emitted by the x-ray tube 55 are concentrated generally between the circumferential grooves 56 and 87, and more specifically are created and accelerated in the region 86 between the anode 83 and the cathode 82. A shield 60 that is composed of a material that effectively and substantially blocks the transmission of x-ray radiation surrounds the entire tube 55. Formed within the shield 60 is a slit 59, the slit 59 overlying the x-ray generation region 86. The slit 59 permits only a plane 48 of x-rays to escape from the region 86 of the tube 55. The tube 55 and shield 60 are mounted within a cooling tank 39, which includes a circumferentially extending gap 47 through which the x-rays admitted through slit 59 can continue to travel as the plane 48 of x-rays continues to spread upwardly generally in the direction of arrow 80. Displaced above the gap 47 at a distance of approximately one foot is the conveyor 3. The conveyor 3 travels generally in the direction of arrow 27, transporting each OUI 78 and 79, for example into the inspection chamber 2. As the plane 48 reaches the conveyor 3, the plane 48 forms a line 81 that is substantially orthogonal to the direction of travel 27, the line 81 identifying the planar slice which passes sequentially through the advancing mass represented by OUI 79.

The tank assembly 38 achieves its rigid structure by means of a series of threaded rods 41 that pass through bores 45 formed within the cathode plate 40 and the anode plate 74, the rods 41 mating with threaded fasteners 42. Connectors 43, 44 and 75 provide electrical access to the interior of the tank assembly 39. Connector 75 provides access to the filament transformer 71, while connector 43 leads to the high voltage feed through insulator 57, which is affixed to the connector 43 by screws 78. Connector 44 leads to the tube socket and heat sink assembly 58, which accepts the plugs or pins 77 formed in the base of tube 55. Although the x-ray tube 55 is intended to emit x-rays generally through the slit 59, stray x-rays may exit the tube 55 from many geometrical orientations. Thus, additional shielding is provided by means of the x-ray shield 72 which is separated from the anode plate 74 by means of standoff 73, and by x-ray shield 50 which is either affixed to the anode plate mount 49 or, in an alternate embodiment, the shield 50 is welded directly to the tube 60.

The interior 70 of the tank assembly 38 is cooled by the circulation of oil, with which the tank 39 can be filled by removing or opening the oil filler cap or valve 46 from the oil filler access port 69. An oil tight seal is provided by o-ring 68. As the tube 55 operates and the oil is heated, the oil necessarily expands. To accommodate the expansion of the oil without exceeding the pressure limits of tank assembly 38, an oil expansion vent 65 is attached to vent port 67 and sealed via o-ring 66. The cap 63 is sealed by o-ring 64. As the oil expands vent chamber accommodates the additional oil volume until a threshold pressure is reached, at which time the vent 62 vents the excess pressure to a safe level. Oil is circulated by means of an impeller 51 which is driven by a brushless motor 53 that is affixed to motor mount 52. The impeller forces oil past a heat sink and fan assembly 207 that further assists the cooling of the tank assembly 38.

Mounted within the inspection chamber 2 and located above both the slit 47 and the OUI 79 is a diode mounting arch 104. Mounting posts 102, which may be mounted to the frame 8 or the inspection chamber 2 by any suitable fastening means, support the mounting arch 104. In most situations the mounting arch 104 will have a width greater than and therefore span the entire width of the conveyor 3, but in other cases can be constructed so as to reside completely above the conveyor thereby permitting a reduction in the width of the arch 104. The photodiode mounting arch 104 supports a series of plates 101 upon which are affixed a plurality of photo diode sensor array boards 91, 92, 93, 94, 95, 96, 97, 98, 99 and 100, each of which includes a photo diode array 103. The actual number of array boards can be selected based on the dimensions of the aperture 7. The number of photo diodes on each board may vary, but in the present example each board 91-100 includes 128 linearly aligned diodes, creating a total linear photodiode sensing array of 1,280 diodes. An x-ray shield 90 resides above the mounting arch 104. The mounting of all of the photo diodes onto the arch 104 permits the rapid removal, replacement and servicing of the entire photo diode sensing portion of the machine 1. Each diode senses the magnitude of the x-ray energy that reaches the diode after being emitted by the x-ray tube 55 and which passes through the conveyor 3 as a plane or sheet 48. At any given moment, some or all of the photodiodes will be receiving energy that has passed only through the conveyor 3 and any associated plastic seals surrounding the aperture, while at other times, as when an OUI 79 intersects the plane 48, some or all of the photodiodes will receive x-ray energy that has been attenuated to varying degrees by the mass and density of the OUI 79.

The novel geometry of the present arrangement of the laterally emitting x-ray tube 55, the OUI 79 and the photodiode mounting arch 104 are several. First, the laterally emitting x-ray tube 55 is able to create a plane 48 having a width that is at least equal to width 105 when reaching the line 81 creating when the plane 48 intersects the plane defined by the conveyor 3. Thus the entire aperture created by the arch 104, as well as any OUI 79 overlying the line 81, is fully illuminated by the x-ray energy exiting the gap 47. This is accomplished at a spacing 88 between the x-ray tube 55 and the conveyor 3 which is substantially less than the spacing that is possible when using a conventional x-ray tube that emits a relatively narrow beam which typically has a beam width on the order of fifteen degrees. The beam width 106 made possible by the laterally emitting x-ray tube 55 is approximately one hundred ten degrees. A second advantage made possible by the close spacing 88 is the relatively small amount of attenuation in the x-ray intensity or flux that occurs by the time the conveyor 3 and OUI 79 are reached by the x-ray plane 48. Thus, for a given x-ray flux, the present arrangement permits the use of a tube 55 having a relatively lower radiated energy and relatively lower power consumption when compared to a conventional longitudinally emitting x-ray tube. A relatively smaller x-ray power supply 32 may be used as compared to a longitudinally emitting x-ray tube. A third advantage permitted by the use of a relatively lower powered, laterally emitting x-ray tube 55 is the reduction in tube cooling requirements, permitting the use of the novel, closed x-ray tank assembly 38 which is able to rely solely on the heat radiating properties of the tank 39 and the oil contained within the tank 39, without the need to replenish or recirculate the oil from an external source. A fourth advantage of the present geometry is that the OUI 79 is surrounded by the photo diode arch 104, which further reduces the dispersion of the emitted x-ray energy prior to reaching a photo diode. By contrast, a longitudinally emitting x-ray tube must be spaced above the conveyor and OUI to accommodate the distance needed to spread the emitted beam throughout the desired aperture, and the photodiode sensors must be limited to a planar array residing beneath the conveyor belt.

Figure 9:
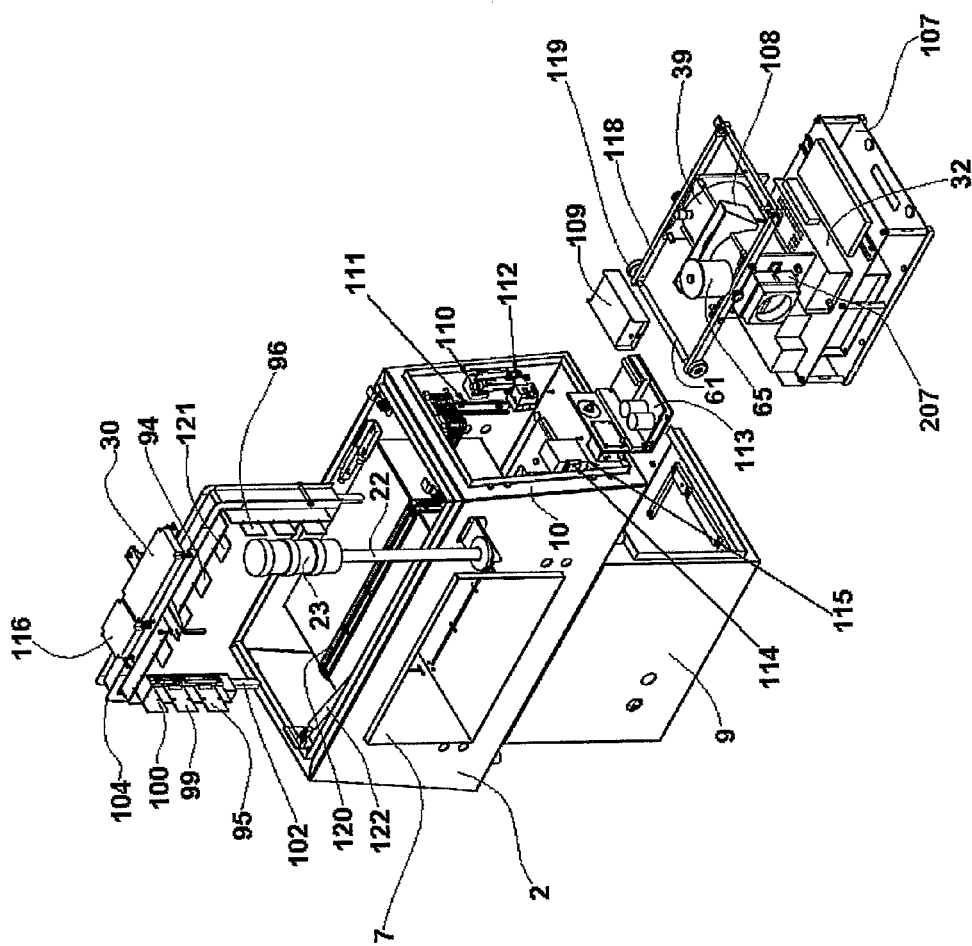
FIG. 9 is a perspective, partially exploded view of the inspection chamber region of the machine depicted in FIG. 1 showing the x-ray tube tank assembly and the photo diode mounting arch displaced from the remainder of the machine.
Figure 10:
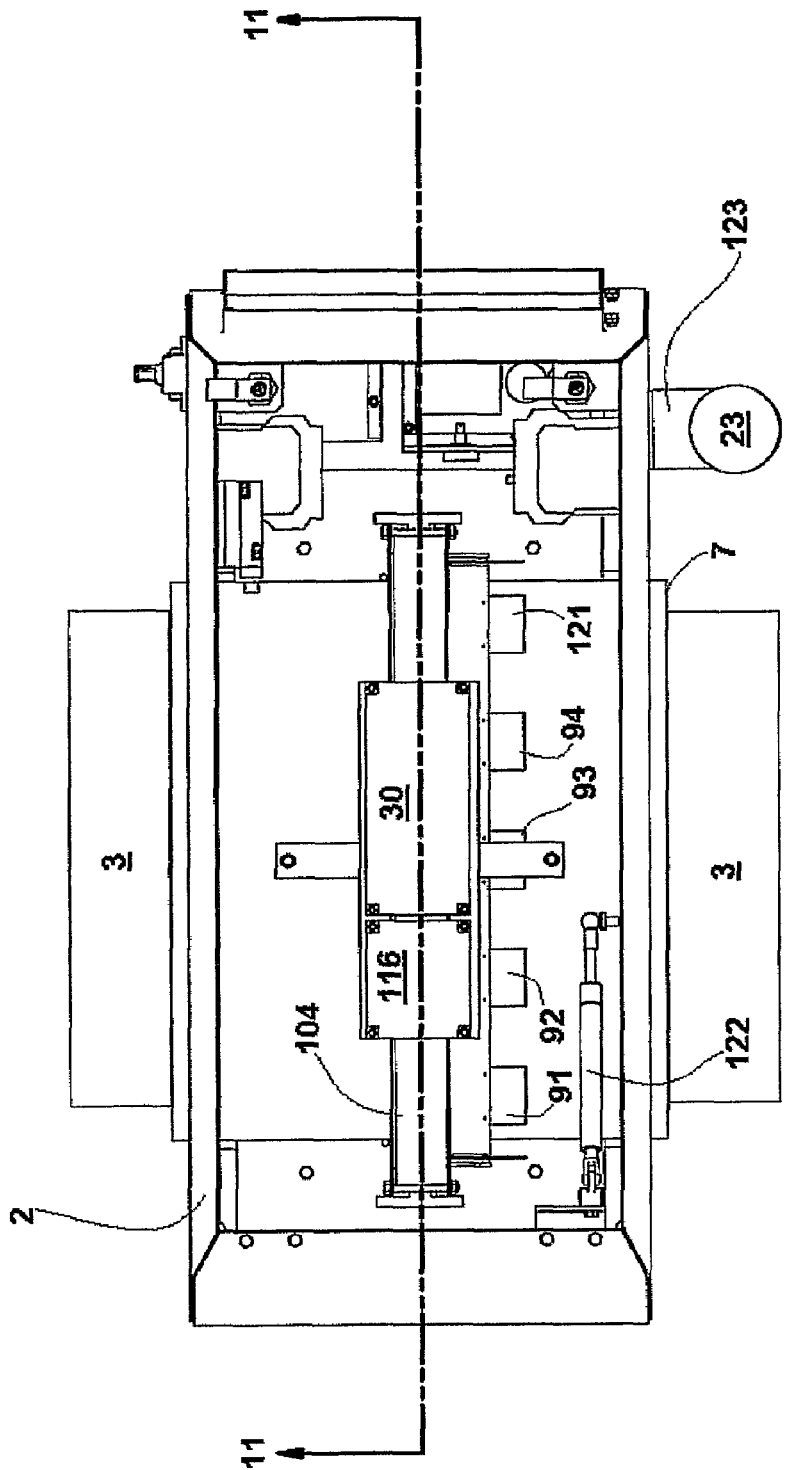
FIG. 10 is a top plan view of the inspection chamber depicted in FIG. 9.
Figure 11:
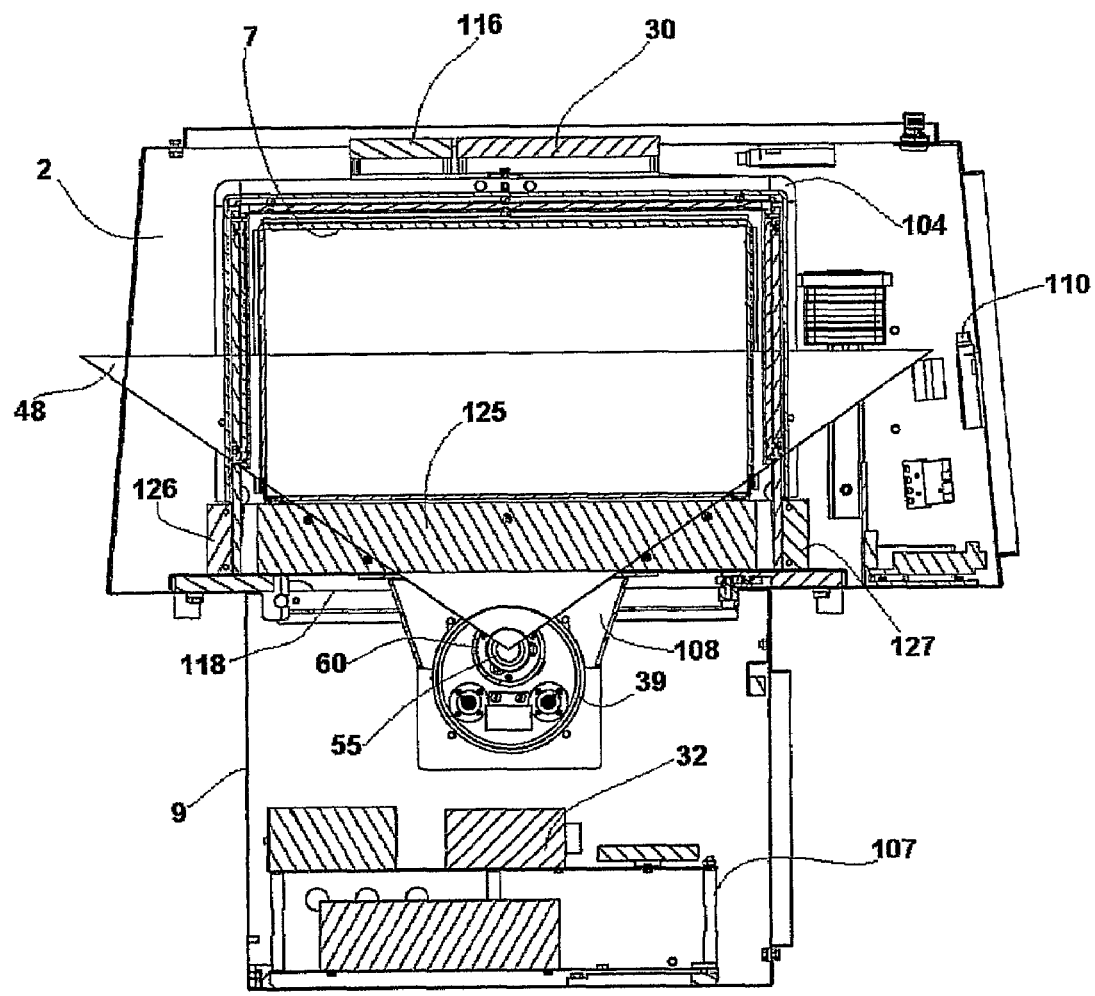
FIG. 11 is a sectional view taken along lines 11-11 as shown in FIG. 10.

Additional features of the inspection chamber 2 are visible with reference to FIGS. 9, 10 and 11. The tank 39 and its associated components are mounted on a tank control assembly 107, which is slidably mounted within the x-ray generation unit housing 9 by means of the frame 118 supported by rollers 119. The x-ray power supply 32 resides on the tank control assembly 107. The tank 39 is seen to include an outer x-ray shield 108 overlying tank emission gap 47 which further insures that the emitted x-ray energy is confined to the plane 48. The data processing module 10 is seen to include the power supply 109 for the liquid crystal display (LCD) 20, a switching power supply 115, a conveyor motor controller 113, an emergency switch disconnector 112, a conveyor start/stop control 110, and a mounting rail assemblies 111 and 114. A slot 120 formed within the aperture 7 permits the emitted x-ray energy contained within plane 48 to reach the photo diode assemblies 94, 96 and 97, for example, residing on the photo diode-mounting arch 104. Mounted on top of the mounting arch 104 is the digital signal processing unit 30 and the image-processing unit 116. A pneumatic strut 122 is attached to the wall of the chamber 2 and assists in raising the chamber lid 21 seen in FIG. 1.

Figure 16:
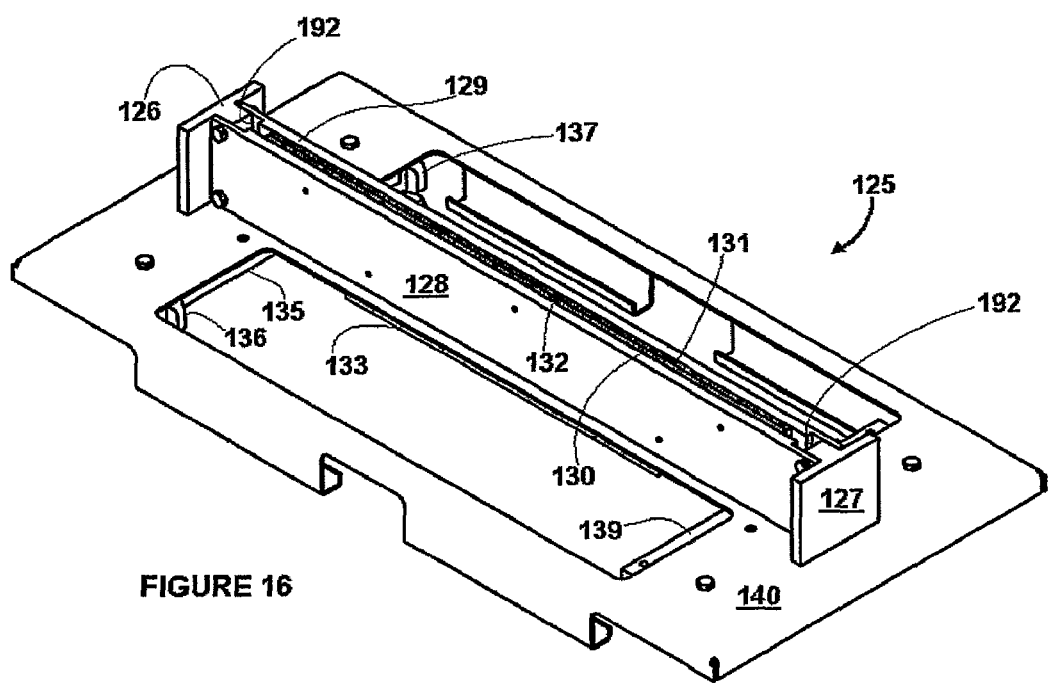
FIG. 16 is a perspective view of the collimator assembly of the machine depicted in FIG. 1.
Figure 17:
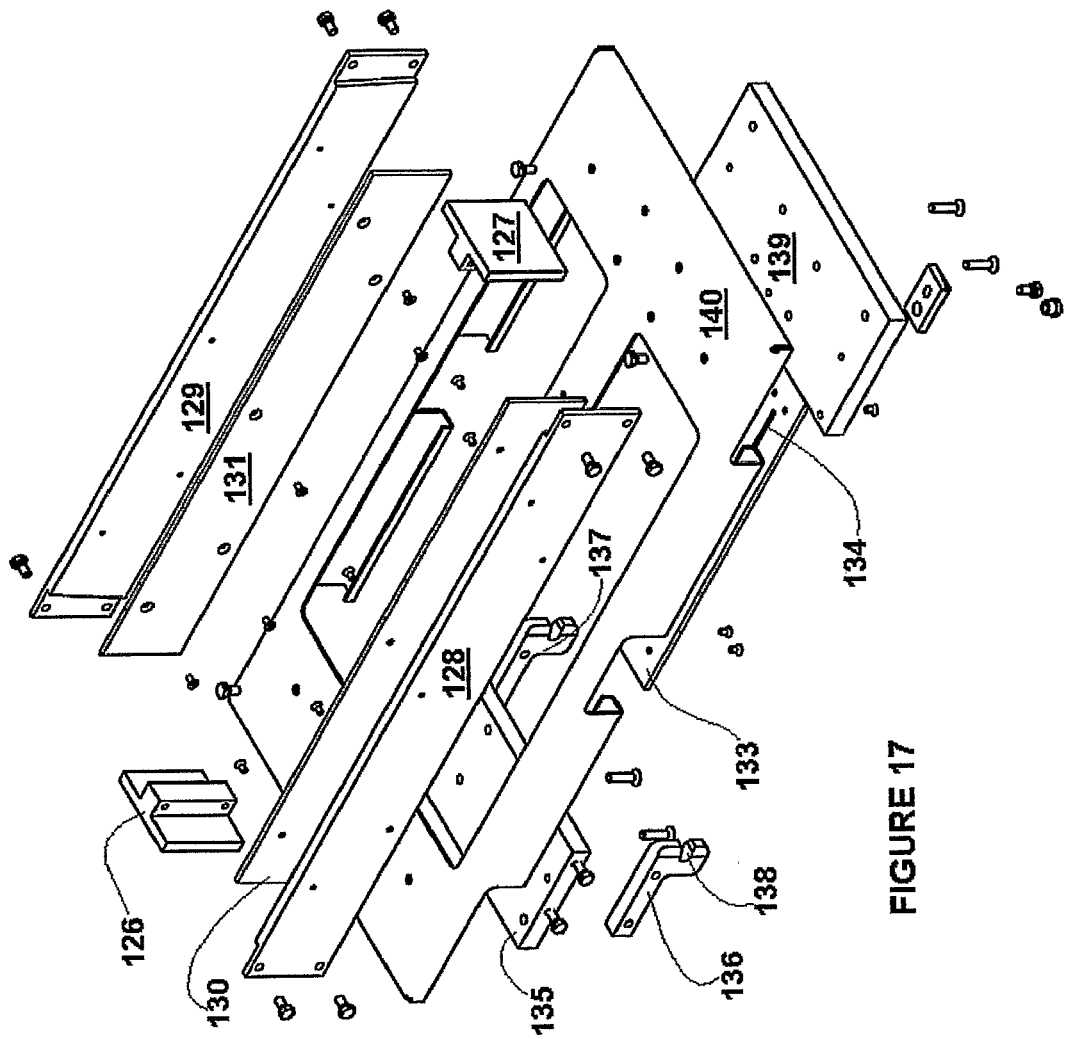
FIG. 17 is an exploded perspective view of the collimator assembly depicted in FIG. 16.

Residing above the outer x-ray shield 108 and directly beneath the lower aperture slot 126 is a collimator assembly 125. As best seen in FIGS. 16 and 17, the collimator assembly 125 includes two end mounting blocks 126 and 127 which, when mounted on the tank mating form 140, together support side supports 128 and 129. Abutting the side support 128 is the vertical collimator shield 130 and abutting the side support 129 is the vertical collimator shield 131, which together create the collimation space or gap 132. A lower collimator shield 133 is affixed to the bottom of the side supports 128 and 129 such that the lower shield slit 134 is aligned in a coplanar fashion with the collimation slot 132. The collimator assembly 125 serves as the mounting point for the x-ray source tank assembly 38. Affixed to the bottom of the mating form 140 are mounting plates 135 and 139. Attached to mounting plate 135 are tank mounting hooks 136 and 137, with similar mounting hooks being affixed to mounting plate 139. Each hook 136, 137 includes a recess 138 adapted to engage the rear rod 61 of the x-ray tank assembly 38 visible in FIG. 9. The collimator assembly 125 thus controls the position of the x-ray source tank assembly 38 so as to allow for straightforward insertion and removal of the tank assembly 38.

The collimator assembly 125 serves as the optical benchmark or foundation for the x-ray machine 1. The assembly 125 locates the photodiode arch 104 such that the assembly 125 resides within or is coplanar with the portion of the emitted x-ray plane 48 that is permitted to pass through the collimator slot 132. The location or registration function is accomplished by means of the receptacles or sockets 192 formed within the collimator assembly 125 adjacent to the intersections of the end mounting blocks 126, 127 and the side supports 128, 129. The lower portions 193 of the arch supports 102 are adapted to be slidably retained within the sockets 192, ensuring that the arch 104 and emitted plane 48 are coplanar, while permitting the arch 104 to be easily removed for servicing, installation and replacement.

Referring also to FIGS. 19 and 20 the structure of the roller assemblies 182 that support the conveyor 3 can be understood. The roller assembly 182 includes a roller 18 which is supported by a tracking block 142. The tracking block 142 supports a bearing mount collar 141 which includes a block engaging surface 183. A central bore 184 accommodates a threaded fastener 146 which secures the bearing 144 within the collar 141. An elongated region 185 formed within the tracking block 142 permits the position of the collar 141, and hence the position of the roller 18, to be slidably adjusted within the tracking block 142. In one embodiment the position of the collar 141 is fixed or secured by means of the cap screw 148 which passes through the bore 150 formed within the tracking block 142. The cap screw 148 continues through a smooth bore 147 formed within the collar 141, thereby permitting the threads of the cap screw 148 to engage the axially aligned threaded bore 186 which is formed in the opposite side of the collar 141.

A pivot pin 143 fits within a bore 149 that is coaxial with the longitudinal axis 187, the bore 149 being formed within the tracking block 142. Referring also to FIGS. 21, 22 and 23, the mounting of the roller assembly 182, as well as the mounting of the slider bed frames 17 and 124, can be better understood. The roller assembly 182 is mounted to the slider bed frame 17 by means of the flip up mounts 151 and 152 which are rigidly affixed to the slider bed frame 17. In one embodiment each flip up mount 151, 152 includes an indentation 153 which is adapted to receive the pivot pin 143 in a stable configuration which, due to the force of gravity, causes the longitudinal axis 188 of the roller 18 to reside at a level that is below the pivot pin axis 187. This arrangement permits the rapid removal or installation of the roller assembly 182 without the use of tools simply by rotating the assembly 182 about the pivot pin 143.

The slider bed frames 17, 124 each include additional components to accommodate the operation of the conveyor 3 and the emission of x-rays through the OUI 79 and toward the photo diode mounting arch 104. The conveyor 3 contacts slider bed surfaces 155, 156 which are mounted on the slider bed frames 124 and 17. Affixed to the slider bed surface 155, for example, are two bed surface mounts 159 and 160. Similarly, bed surface mounts 161 and 162 are affixed to the slider bed surface 158 adjacent to leading edge 163. As best seen in FIGS. 24 and 25, the bed surface mount 160 includes a standoff 175 that supports a block 176 by means of fastener 178. The block 176 is formed to include a groove 177 that is adapted to receive a rod 174 that is formed within the underside of the slider bed surface 155. The rod 174 is thus slidably received into the grooves 173 and 177 of the bed surface mounts 159 and 160, respectively. Also affixed to the surface of the slider bed 124 are extended slider bed mounts 170 and 171 which include a standoff 180 that is secured to block 191 by means of threaded fastener 179. Similarly, the slider bed surface 158 includes extended slider bed mounts 164 and 167 mounted adjacent to trailing edge 166. Extending between each block 191 is a shaft 169, with shaft 165 being similarly configured above slider bed surface 158. Formed within each block 191 is a groove 181 adapted to receive a rod 189 that is formed within the underside of the slider bed surface 155. The slider bed surface 155 is capable of pivoting movement about the rod 174 in the directions indicated by the arrow 190. The slider bed surface 155 may be installed by placing the rod 174 within the grooves 173 and 177 and lowering the surface 155 until the shaft 189 engages the grooves 181. Access to the slider bed surfaces 155 and 156 is accomplished by lifting the lids 16 and 25, which is assisted by pneumatic strut 154, for example. When in an operative position, the leading edge 172 of slider bed surface 155 and the leading edge 168 of the slider bed surface 156 are separated by a small gap that is slightly greater than the gap 126 formed within the bottom of the aperture 7, thereby permitting the x-ray plane 48 to pass between the opposed slider bed surfaces 155 and 156.

Although the laterally emitting x-ray tube 55 and its associated power supply 32 generate less heat than previous x-ray based metal detectors, the heat generated is nonetheless substantial. In order to preserve the small size and relative simplicity of the machine 1 that is afforded by the novel geometry of the x-ray tube 55 and the photo diode mounting arch 104, a novel cooling system is employed. Referring also to FIGS. 6, 7, 8 and 12, the cooling system of the machine 1 can be better understood. The machine 1 includes a vortex type of cabinet cooler of the type generally disclosed, for example, in U.S. Pat. No. 2,790,310, entitled AXIAL FLOW VORTEX TUBE MECHANISM, issued to Green on Apr. 30, 1957. While vortex generators are useful for cooling many types of enclosures, they have traditionally been unsuitable for enclosures having barriers which impede the flow of cool air, such as barriers within the machine 1 including, for example, the inspection tunnel within chamber 2, the tank 39 and the tray 107. In order to utilize the advantages of a vortex tube despite the presence of barriers within the machine 1, a separate exhaust 193 for heated air 194 is provided near the top of the inspection chamber 2, approximately at the level of the lamp mounting bracket 123. Further, a sealing installation unit adapter 199 is used to accomplish the transition of the vortex tube 198 into the interior of the x-ray generation unit housing 9. In order to prevent the ingress of dust and moist outside air into the x-ray generation unit housing 9, a small positive pressure, on the order of 0.25 pounds per square inch (psi), is supplied by the addition of a filter 203 in series with the exhaust 193. Air flow resistance of the filter 203 is sufficient to create the small positive pressure required.

The sealing installation unit adapter 199 includes a seal or o-ring 200, fitting 197, and muffler 54, the body of which functions as a directional channel. The hot air exhausts the vortex tube 198 at exhaust port 196. Pressurized air 195 enters the vortex 198 at air inlet 204. The cold air 195 enters the muffler 54 and is directed toward the opposite interior wall 201 of the x-ray generation unit housing 9. The air is divided by the wall 201 into two paths 205 and 206. The upward cool air path 205 is captured by the tank fan 207, while the downward cool air path is captured by the skid fan 202. The air contained within the upward cool air path 205 is further driven upwardly by natural convection due to the rising of heated air and also the air pressure drop that is encountered as the approximately 6.0 bar air entering housing 9 moves in the direction of the aperture 7 and finally exits through filtered exhaust port 193. This air circulation further provides heat exchange and cooling of the sealed x-ray detector sealed region surrounding photo diode mounting arch 104.

Figure 30:
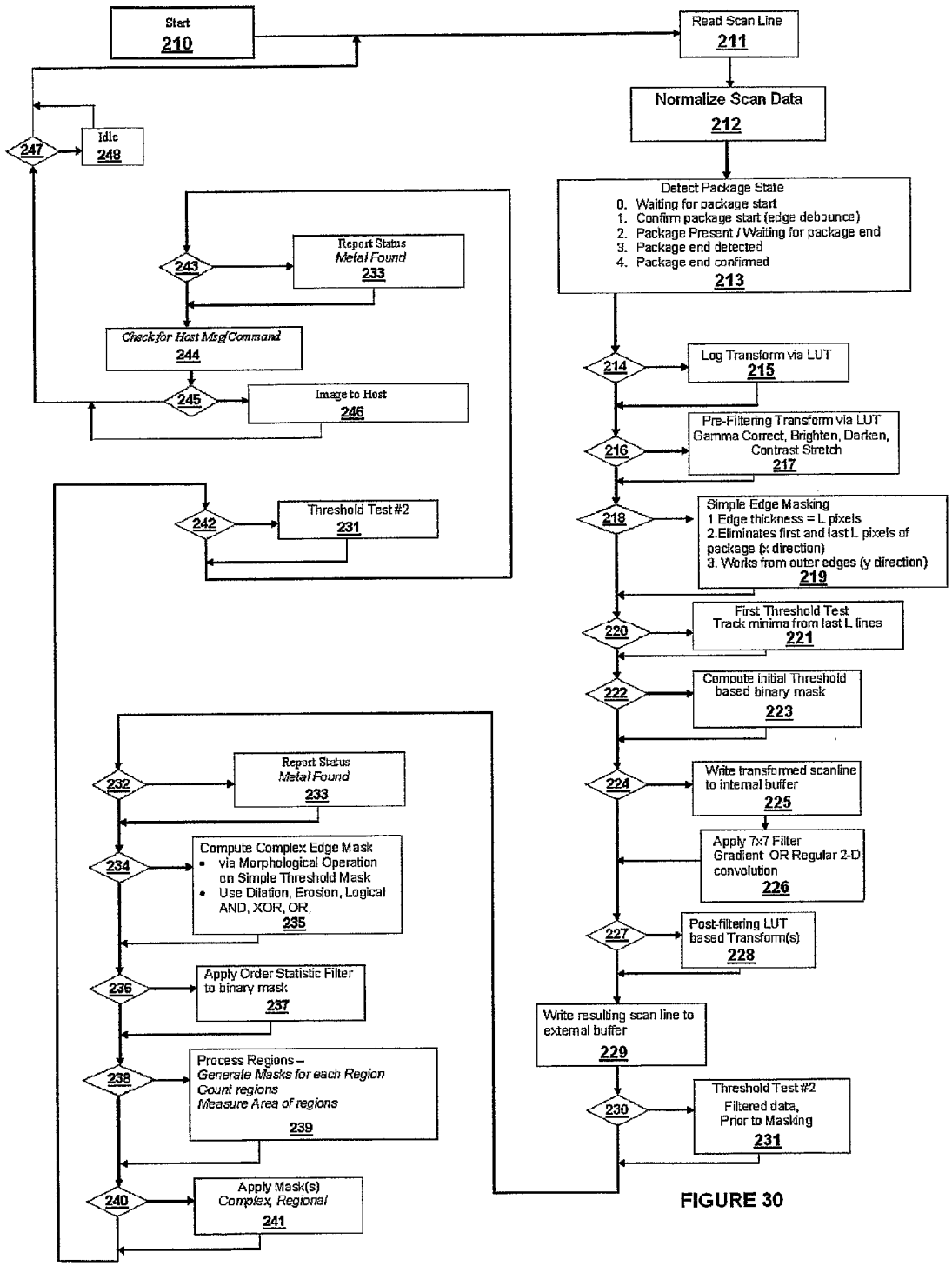
FIG. 30 is a flowchart depicting signal processing as performed by the machine depicted in FIG. 1.

Given the general layout of the machine 1 that has now been discussed, the actual processing of an OUI 79 can be better appreciated with reference to FIG. 30. The contaminant detection process starts at step 210, at which time the machine 1 is operating and the conveyor 3 is transporting an OUI 79 so as to intersect the emitted x-ray plane 48 and cause the photo diodes mounted on arch 104 to receive x-ray radiation. The initial task is to acquire the photo diode data, which begins at step 211 with IPU 116 reading the scan line produced by the A/D module 29. The linear array of photo diodes mounted on arch 104 measures the intensity of x-ray radiation that impinges each individual photo diode. The output of each diode is correlated to its position on the arch 104, thereby producing a line of photo diode data. Typically, each line of photo diode data is read approximately one thousand times per second, with the width of each scan line corresponding to a width of 0.8 millimeters. Thus, the optimum speed of conveyor 3 is approximately 48 meters per minute. At step 212 the raw scan line data produced by the A/D module 29 is normalized by the IPU 116 according to the formula $$(\text{data}(k)-\text{offset}(k))*\text{gain}(k),$$

where k is an index representing diode location as determined by the DSP 30. Each diode is individually compensated for gain and effect. At step 213, the physical position of the OUI 79 is monitored and a value is assigned to each possible state. For example, a zero signifies that the OUI is not within the plane 48, a one confirms that the leading edge of the OUI 79 has reached plane 48, a two indicates that the OUI 79 is present and is moving through the plane 48, a three indicates that the trailing edge of the OUI 79 has been detected and a four indicates that the OUI 79 has left the plane 48. The status of OUI 79 is continuously monitored at step 214, and whenever the OUI is present the image processing, and hence the contaminant detection process, is conducted on a line by line basis, beginning at step 215. The data corresponding to a complete line of photo diode detection levels is first transformed into the corresponding logarithms via a look up table at step 215. After verifying the integrity of the data at step 216, the logarithmic data produced at step 215 is subjected to a prefiltering transform 217 via a look up table, such transforms including, for example, gamma correction, brightening, darkening and contrast stretching. After verifying the presence of data at step 218, the simple edge-masking filter 219 is applied to each line of data as the A/D converter 29 is producing the line data. The edge thickness, when available, is assigned a value of L pixels, and the first and last L pixels are removed from the line data in the "X", or line length direction, with the process continuing in the "y", or line width direction indicated by arrow 27. Assuming that this process produces valid data at step 220, the first contaminant threshold test 221 is performed based on minimum values obtained from the last L lines. After this data is verified at step 222, the initial threshold based binary mask is computed at step 223. After verifying the mask data at step 224, the transformed scan line data is written to an internal buffer at step 225 and then processed by either a 7×7 gradient filter or a regular two-dimensional convolution at step 226. The resultant data is verified at step 227 and subjected to additional post filtering look up table based transforms at step 228 before being written to an external buffer at step 229. Step 230 transfers the resulting scan line to a second threshold test 231 that is applied to the filtered data prior to masking.

Steps 215-231 comprise the contaminant detection process sequence that is applied to each individual scan line produced by the photo diode sensor array 28. If any of the line scanning operations produces an indication of a contaminant in the OUI 79, step 232 forwards this as a status report 233. Regardless of the line scanning results, a second scan of the complete image composed of all the lines associated with OUI 79 is performed, beginning at step 234, which forwards the complete image data to the complex edge mask computer 235. The image complex edge mask is computed by performing a morphological operation on the simple threshold mask, and by the use of dilation, erosion and logical AND, XOR and OR operations. At step 236 the complete image data is forwarded to the order statistic filter computer 237, which applies an order statistical filter to the binary mask. At step 238 the complete image data is forwarded to the regional computer 239, which generates masks for each region, counts each region and also measures the area of each region. Once all of the masks have been created, step 240 forwards the complete image data to the mask application computer 241 that applies each of the completed masks. At step 242 the unfiltered complete image data is subjected to the second threshold test 231 prior to masking. If complete image processing steps 232-242 produce a contaminant indication for OUI 79, step 243 initiates the contaminant present indication 233. After each OUI 79 is processed, a check for commands from the computer 31 is accomplished at step 244. The completed image, if contaminated, is forwarded to the computer 31 at step 246. The absence of additional image data is sensed at step 247 and the image processing is put in an idle state 248 until additional data is received.

Figure 13:
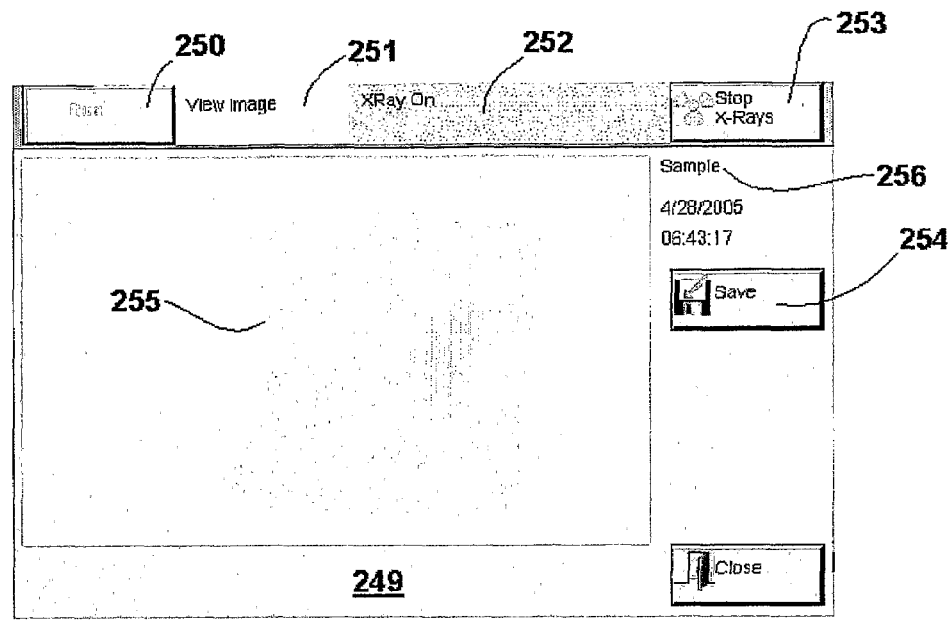
FIG. 13 is a sample package graphical user interface (GUI) of the machine depicted in FIG. 1.
Figure 14:
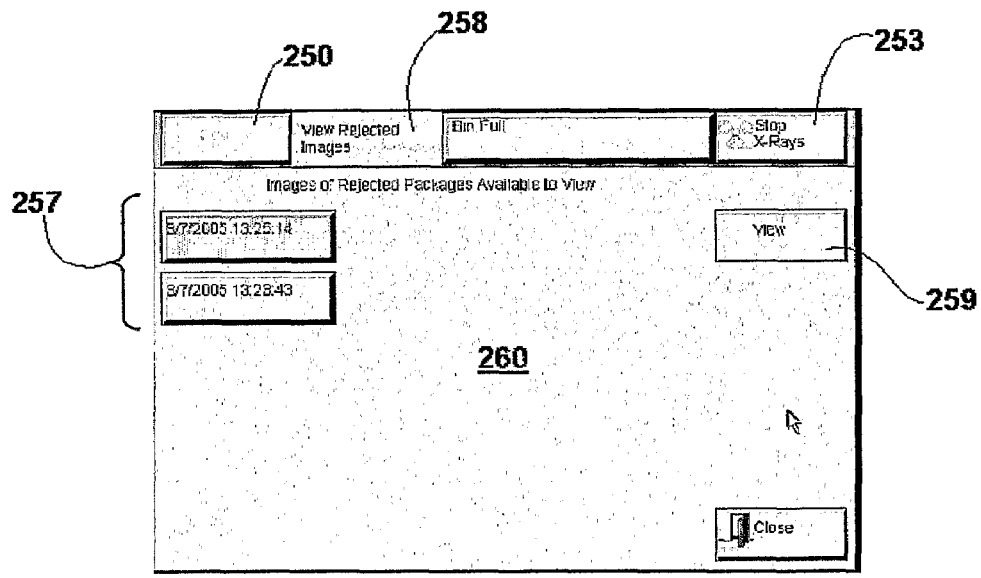
FIG. 14 is the rejected image GUI of the machine depicted in FIG. 1.
Figure 15:
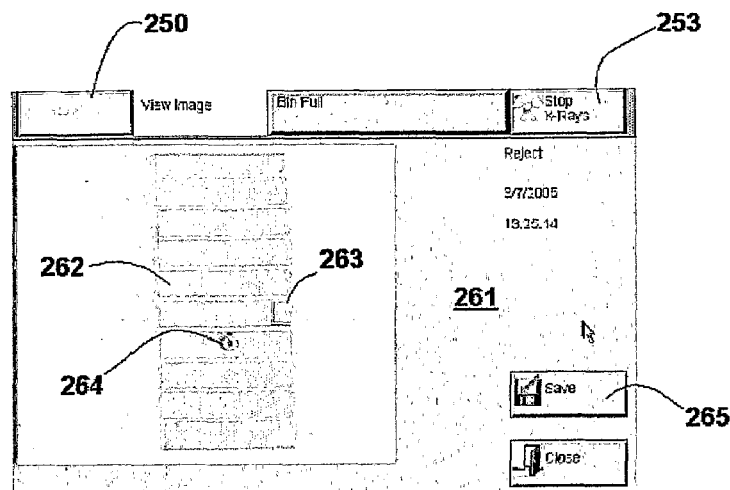
FIG. 15 is an example of a rejected product image available via the GUI depicted in FIG. 14.

A user of the machine 1 has access to the control and operation of the machine by means of the display panel 20 that presents the user with a graphical user interface 249, as seen in FIG. 13. The GUI 249 is displaying, for example, the run screen 250, from which the user has selected the sample package option 256. When the sample package option 256 is selected, the next OUI 79 crossing the plane 48 is displayed as an image 255 after being completing image-processing steps 232-242. The view image tab 251 is accordingly highlighted, as is the x-ray "on" tab 252. The image 255 can be saved by selecting the save button 254. The user can stop the emission of x-rays at any time by selecting the stop button 253. The machine 1 gives the user the ability to view as many as nine images of rejected OUIs by means of the GUI 260 illustrated in FIG. 14. The tab 258 indicates that the user has selected the view rejected images option from the run screen 250. The tab 257 indicates the date and time of the rejected images. Selecting the view tab 259 accesses the GUI 261 depicted in FIG. 15. The selected image 262, and the suspected contaminants 263 and 264, can be viewed. The save tab 265 permits the user to save the image 262 if desired.

Figure 31:
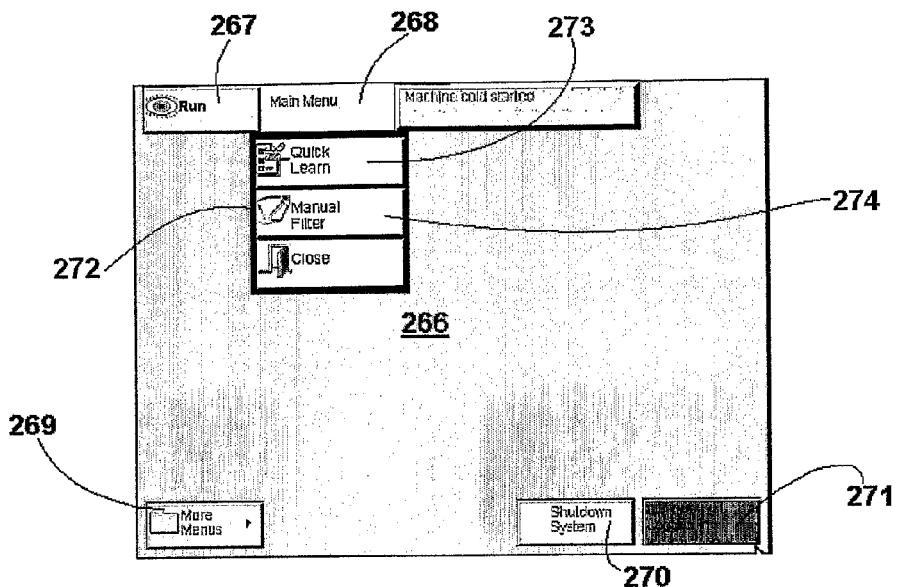
FIG. 31 is the main screen graphical user interface (GUI) of the machine depicted in FIG. 1.
Figure 32:
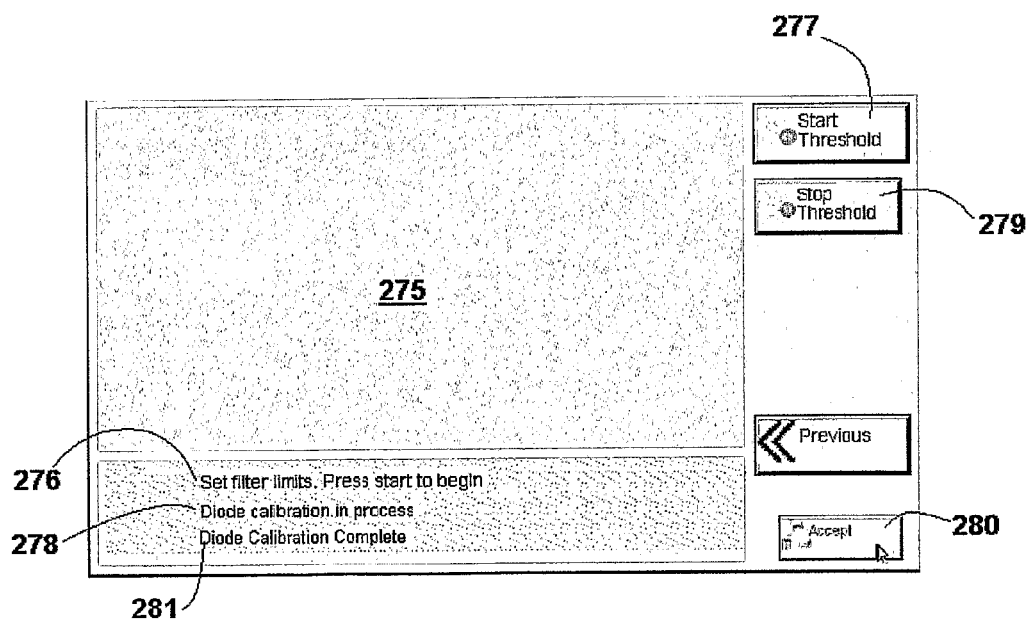
FIG. 32 is the automatic filter selection GUI of the machine depicted in FIG. 1.
Figure 33:
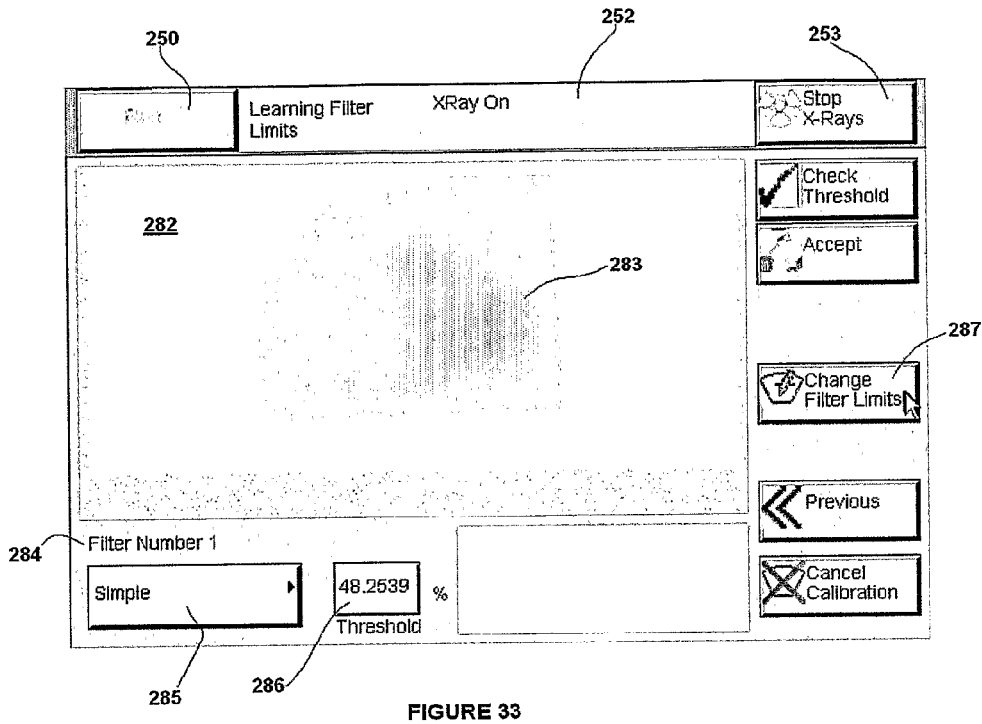
FIG. 33 is the change filter limits GUI of the machine depicted in FIG. 1.
Figure 34:
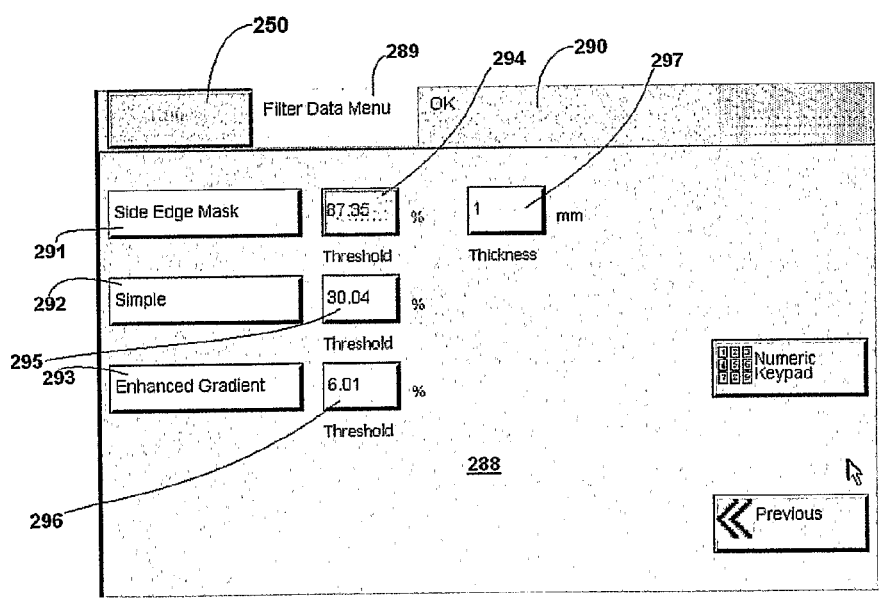
FIG. 34 is the manual filter GUI of the machine depicted in FIG. 1.

The main screen GUI 266 is depicted in FIG. 31, and is the first screen presented after a user 271 logs onto the machine 1. Tab 267 provides access to the run screen 250, while tab 268 provides access to the main menu. More menus can be accessed via tab 269, and the machine 1 can be shut down by means of tab 270. An example of a drop down menu is the filter selection menu 272, which permits the user to choose either automatic filter selection 273 or manual filter selection 274. Choosing automatic filter selection accesses the "quick learn" GUI 275, which selects the default filter configuration starting with a given size for aperture 7 and a given speed for conveyor belt 3. Message 276 invites the user to begin the filter limit selection process by pressing the start threshold button 277, which causes the diode calibration in progress message 278 to be displayed. Once the diode calibration complete message 281 appears, the stop threshold button 279 is pressed. The machine 1 is now in verification mode. The user is then able to pass both contaminated and uncontaminated OUIs 79 through the aperture 7. If the automatically selected the filter settings are able to detect contaminated product without false indications appearing for uncontaminated products, the user is able to select the accept button 280. In the event that the user wishes to alter the filter limits, one embodiment of the present invention permits the user to access the change filter limits GUI 282 illustrated in FIG. 33 by activating the change filter limits button 287. By selecting the button 287, the user obtains access to several data items that now appear on the GUI 282, such as the filter number 284, the filter type 285 and the threshold value 286. If the user wishes to set all of the filter parameters manually, the manual filter GUI 288 may be accessed, which displays a filter menu 289. Each type of available filter, such as the side edge mask filter 291, the simple filter 292 and the enhanced gradient filter 293 is displayed. Each filter displays a corresponding threshold such as thresholds 294, 295 and 296, for example. If a side edge mask filter is chosen, the thickness 297 of the side edge mask is displayed. The user may alter the threshold values and accept the choices by selecting the "OK" button 290.

Figure 26:
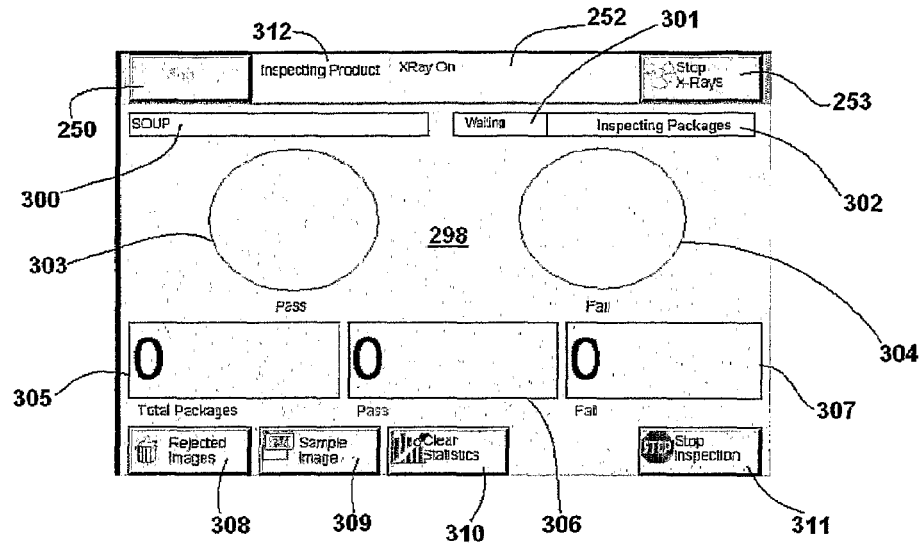
FIG. 26 is the start inspection GUI of the machine depicted in FIG. 1.
Figure 27:
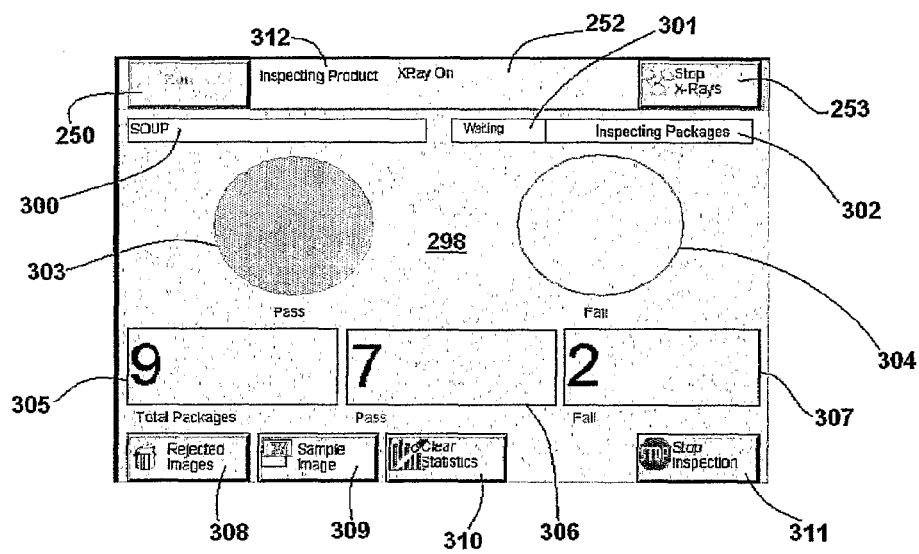
FIG. 27 is the passed product GUI of the machine depicted in FIG. 1.
Figure 28:
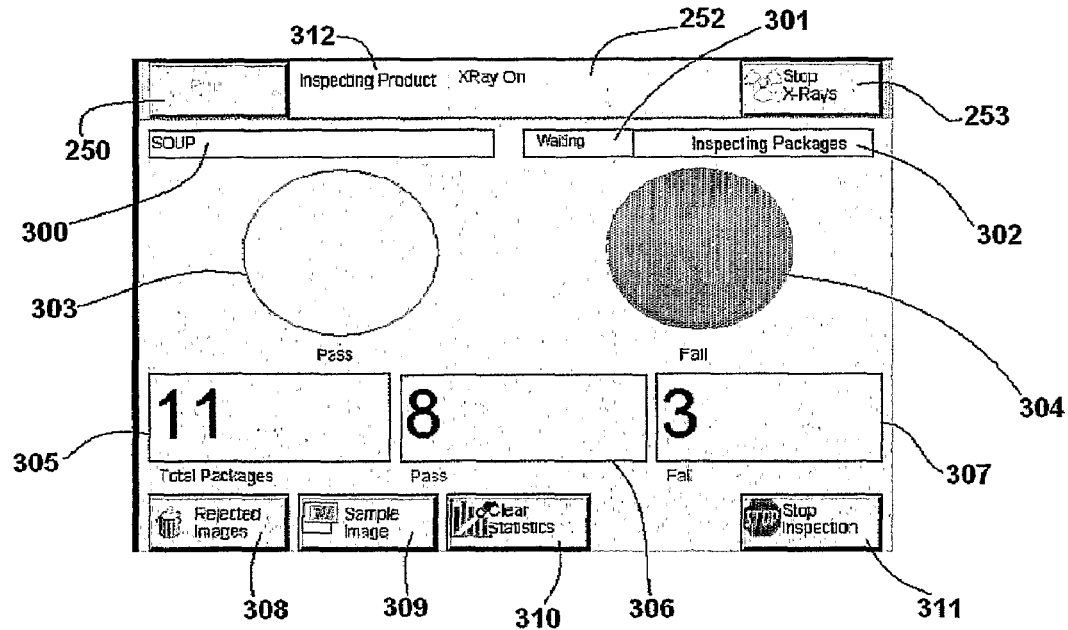
FIG. 28 is the failed product GUI of the machine depicted in FIG. 1.

Once the filter selections and calibration have been completed, the operator of the machine 1 can begin the routine inspection of OUIs 79 by accessing the start inspection GUI 298 illustrated in FIG. 26. The inspecting product status bar 312 is displayed, and an OUI may be placed on the conveyor 3. The type of OUI is displayed in box 300. The waiting for x-rays box 301 is displayed until x-ray emissions actually begin, at which time the inspecting packages box 302 is activated and an OUI 79 may be conveyed through the aperture 7 for inspection. An uncontaminated package will activate pass indicator 303 and a contaminated product will activate fail indicator 304. The total number of packages processed is displayed in box 305, the total number of uncontaminated products is displayed in box 306 and the total number of contaminated products is displayed in box 307. The image of a rejected package can be displayed by pressing button 308, and button 309 allows the operator to sample a package and store the inspection data as an image. The clear statistics button 310 permits an operator to zero the values in boxes 305, 306 and 307. The operator can stop the inspection process and turns off the x-ray beam by pressing button 311. As seen in FIG. 27, a passed product completely fills the pass indicator 303, and as the inspection process continues the statistics boxes 305, 306 and 307 are valued. Referring also to FIG. 28, the presence of a contaminated product is seen to completely fill the fail indicator 304.

The invention is not limited to the foregoing description of the machine 1. Numerous modifications consistent with this disclosure are possible. For example, the position of the tank assembly 38 may be adjusted by means of a motor which would permit adjustment of the alignment between the emitted plane 48 and the collimation slot 129. The physical size of the photo diodes, as well as the dimensions of the mounting arch 104, may also be reduced for machines having a smaller aperture 7 to incorporate finer spatial sampling. The computer 31 may incorporate weighing algorithms to provide a net content value for each OUI 79. The IPU 116 may be advantageously modified to provide a faster image processing cycle, thereby permitting the conveyor 3 to operate at a higher speed and to provide greater contaminant detection sensitivity. These as well as other modifications are within the scope of the appended claims.

We claim:

1. A contaminant detector (1) for detecting dense contaminants within a food product, the contaminant detector having an x-ray beam emitting vacuum tube (55) and a substantially horizontal conveyor belt (3) adapted to transport a food product through the x-ray beam characterized in that:
   the vacuum tube (55) has a longitudinal axis and emits a substantially planar x-ray beam (48) in an upward direction that is substantially orthogonal to the longitudinal axis (64) of the vacuum tube;
   the conveyor belt (3) is located above the x-ray generator;
   an array of photo diodes (28) is located above the conveyor belt, the array of photo diodes being adapted to intercept x-ray energy that has passed through the food product, wherein a first greatest distance (88) between the x-ray generator and the conveyor belt and a second greatest distance (89) between the conveyor belt and the array of photo diodes is approximately equal;
   a tank assembly (38), the tank assembly being adapted to enclose the vacuum tube (55), wherein the tank assembly comprises:
       a heat absorbing liquid;
       an impeller (51), the impeller being adapted to circulate the heat absorbing liquid within the tank assembly;
       a heat sink, the heat sink being mounted adjacent to the impeller and being isolated from the heat absorbing liquid;
       a fan (207), the fan being mounted adjacent to the heat sink and being isolated from the heat absorbing liquid such that heat is transferred from the vacuum tube to the heat absorbing liquid to the heat sink to atmospheric air being transported across the heat sink by the fan;
       a vortex cooler (198);
       a cabinet (9), the cabinet housing the tank assembly (55); and
       a vortex cooler adapter (199), the vortex cooler adapter being affixed to the cabinet, the vortex cooler adapter having a first end attached to the vortex cooler and a second end attached to a channel that directs relatively cool air entering the vortex cooler into an interior region of the cabinet, thereby maintaining a positive air pressure within the cabinet,
   wherein the array of photo diodes is mounted on a rigid arch (104) such that approximately two hundred seventy degrees of a perimeter of the food product residing within the substantially planar x-ray beam (48) resides between the x-ray generator (55) and at least one photo diode (91, 92, 93, 94).

2. The contaminant detector of claim 1, further comprising a collimator, the collimator comprising:
   a collimation gap (132), the collimation gap residing within the substantially planar x-ray beam (48) between the x-ray generator (55) and the conveyor belt (3);
   a pair of receptacles (192) adapted to receive a portion of the rigid arch supporting the photo diodes such that the photo diodes are optically aligned with the substantially planar x-ray beam;
   a computer (31), the computer being programmed to cause the array of photo diodes to repeatedly scan the food product while the food product is being conveyed through the substantially planar x-ray beam so as to produce a series of discrete lines of received x-ray intensity data;
   an image processing unit (116), the image processing unit being adapted to examine each discrete line of received x-ray intensity data for an indication of a contaminant within the food product; and
   a digital signal processor (30), the digital signal processor being adapted to receive instructions from the computer regarding at least one of a) object characteristics, b) contaminant characteristics, c) object location with respect to the x-ray sensor array, and d) a sequence of operations to be performed by the digital signal processor, the digital signal processor being adapted to deliver operating commands to the x-ray sensor array regarding x-ray sensor operation including at least one of a) scan rate, b) gain and c) integration time.

3. The contaminant detector of claim 2, wherein the image processing unit (116) is adapted to create a complete image of a scanned food product by sequentially mating each discrete line of received x-ray intensity data, the image processing unit being adapted to examine the complete image for an indication of a contaminant within the food product.

4. The contaminant detector of claim 3, wherein the computer (31) is adapted to select at least one digital filter to be applied by the image processing unit when the image processing unit is examining received x-ray intensity data from the array of photo diodes (28).

5. The contaminant detector of claim 4, wherein the image processing unit (116) is adapted to process a single batch of data corresponding to a single scan line of the object produced by the array of photodiodes (28) and determine a likelihood of contaminant presence within the object based on an analysis of the single batch of data.

6. The contaminant detector of claim 5, wherein the image processing unit (116) is adapted to create an image of the object by combining a plurality of single scan line batch data so as to create multiple lines of adjoining data which form an image of the object, the image processing unit being adapted to analyze the image of the object to ascertain a contaminant presence within the object.

7. The contaminant detector of claim 1, further comprising:
   two slider bed surfaces (157, 158), each slider bed supporting a portion of the conveyor belt (3), each slider bed surface being substantially planar and being substantially orthogonal to the substantially planar x-ray beam (48), the slider bed surfaces being arranged in an opposed, spaced apart relationship such that an emission plane formed by the substantially planar x-ray beam is able to pass between the two slider bed surfaces.

8. The contaminant detector of claim 7, wherein each slider bed surface further comprises:
   a first edge (163);
   a second edge (166);
   a first rod (174) formed adjacent to the first edge; and
   a second rod (189) formed adjacent to the second edge, wherein the first rod is adapted to engage a first indention (177) on the contaminant detector and pivot with respect to the first indentation, the second rod being adapted to engage a second indented surface (181) on the contaminant detector so as to prevent rotation of the first rod with respect to the first indentation, thereby securing the slider bed surface in a fixed position.

* * * * *